US010822368B2

(12) United States Patent
DeRosa et al.

(10) Patent No.: US 10,822,368 B2
(45) Date of Patent: *Nov. 3, 2020

(54) RIBONUCLEIC ACIDS WITH 4'-THIO-MODIFIED NUCLEOTIDES AND RELATED METHODS

(71) Applicant: TRANSLATE BIO, INC., Lexington, MA (US)

(72) Inventors: Frank DeRosa, Lexington, MA (US); Michael Heartlein, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/282,106

(22) Filed: Feb. 21, 2019

(65) Prior Publication Data

US 2019/0263850 A1   Aug. 29, 2019

Related U.S. Application Data

(63) Continuation of application No. 14/776,506, filed as application No. PCT/US2014/027422 on Mar. 14, 2014, now Pat. No. 10,266,559.

(60) Provisional application No. 61/785,098, filed on Mar. 14, 2013.

(51) Int. Cl.
C12N 15/67    (2006.01)
C07H 21/02    (2006.01)

(52) U.S. Cl.
CPC ............. *C07H 21/02* (2013.01); *C12N 15/67* (2013.01)

(58) Field of Classification Search
None
See application file for complete search history.

(56) References Cited

U.S. PATENT DOCUMENTS

| | | | |
|---|---|---|---|
| 5,441,868 A | 8/1995 | Lin | |
| 5,639,873 A | 6/1997 | Barascut et al. | |
| 2005/0130923 A1 | 6/2005 | Bhat et al. | |
| 2010/0015218 A1 | 1/2010 | Jadhav et al. | |
| 2011/0244026 A1* | 10/2011 | Guild ................ | A61K 48/0008 424/450 |
| 2013/0115272 A1 | 5/2013 | De Fougerolles et al. | |
| 2015/0167017 A1 | 6/2015 | Roy et al. | |
| 2016/0237108 A1 | 8/2016 | Fraley et al. | |
| 2016/0264614 A1 | 9/2016 | Conlee et al. | |
| 2016/0304552 A1 | 10/2016 | Roy et al. | |

FOREIGN PATENT DOCUMENTS

| | | |
|---|---|---|
| WO | WO 2005/027962 A1 | 3/2005 |
| WO | WO 2011/006810 A2 | 1/2011 |
| WO | WO 2012/170930 A1 | 12/2012 |
| WO | WO 2015/051169 A2 | 4/2015 |
| WO | WO 2015/051173 A2 | 4/2015 |
| WO | WO 2015/089511 A2 | 6/2015 |
| WO | WO 2016/164762 A1 | 10/2016 |

OTHER PUBLICATIONS

GenBank AB208800.1, 2016, pp. 1-3 (Year: 2016).*
Anderson, B. R., et al., "11 Nucleoside modifications in RNA limit activation of 2'-5'-oligoadenylate synthetase and increase resistance to cleavage by RNase," Nucleic Acids Research, vol. 39, No. 21, Nov. 1, 2011 (Nov. 1, 2011), pp. 9329-9338.
Bellon et al., "Sugar modified oligonucleotides: Synthesis, nuclease resistance and base pairing of oligodeoxynucleotides containing 1-(4'-thio-β-d-ribofuranosyl)-thymine," Biochemical and Biophysical Research Communications, 1992, vol. 184, No. 2, pp. 797-803.
Bellon et al., "4'-Thio-oligo-β-D-ribonucleotides: synthesis of β-4'-thiooligouridylates, nuclease resistance, base pairing properties, and interaction with HIV-1 reverse transcriptase," Nucleic Acids Research, 1993, vol. 21, No. 7, pp. 1587-1593.
Culver, "Meanderings of the mRNA through the Ribosome," Structure, vol. 9, 751-758 (2001).
Dande, P., et al., "Improving RNA interference in mammalian cells by 4'-thio-modified small interfering RNA (siRNA): effect on siRNA activity and nuclease stability when used in combination with 2'-O-alkyl modifications," Journal of Medicinal Chemistry, American Chemical Society, US, vol. 49, No. 5, Mar. 9, 2006 (Mar. 9, 2006), pp. 1624-1634.
Debus, H., et al., "Delivery of messenger RNA using poly(ethylene imine)-Poly(ethylene glycol)-copolymer blends for polyplex formation: Biophysical characterization and in vitro transfection properties," Journal of Controlled Release, 148:334-343 (2010).
Demeshkina, N., et al., "Interactions of the ribosome with mRNA and tRNA," Current Opinion in Structural Biology, Elsevier Ltd, GB, vol. 20, No. 3, Jun. 1, 2010 (Jun. 1, 2010), pp. 325-332.
Haeberli et al., "Syntheses of 4'-thioribonucleosides and thermodynamic stability and crystal structure of RNA oligomers with incorporated 4'-thiocytosine", Nucleic Acids Research, 2005, vol. 33, No. 13, pp. 3965-3975.
Hoshika, S., et al., "Investigation of physical and physiological properties of 4'-thioribonucleotide (4' thioRNA)," Nucleic Acids Research Supplement, No. 3, 2003, pp. 209-210.
Hoshika, S., et al., "Synthesis and physical and physiological properties of 4'thioRNA: application to post-modification of RNA aptamer toward NF-kB," Nucleic Acids Research, 2004, vol. 32, No. 13, pp. 3815-3825.
Huttenhofer, A., and Noller, H.F., "Footprinting mRNA-ribosome complexes with chemical probes," The EMBO Journal, vol. 13, No. 16, Jan. 1, 1994 (Jan. 1, 1994), pp. 3892-3901.

(Continued)

Primary Examiner — Ekaterina Poliakova-Georgantas
(74) Attorney, Agent, or Firm — Proskauer Rose LLP; Fangli Chen; Christine G. Espino

(57) ABSTRACT

Disclosed are messenger RNA molecules and related compositions incorporating a 4'-thio modification in the furanose ring of at least one nucleotide residue, and methods of using these mRNAs to produce an encoded therapeutic protein in vivo and to treat or prevent diseases or disorders. In certain embodiments, the 4'-thio modified mRNA provides for enhanced stability and/or reduced immunogenicity in in vivo therapies.

17 Claims, 4 Drawing Sheets

Specification includes a Sequence Listing.

(56) References Cited

OTHER PUBLICATIONS

Jones, G. D., et al., "Duplex- and triplex-forming properties of 4'-thio-modified oligodeoxynucleotides," Bioorganic & Medicinal Chemistry Letters, Pergamon, Amsterdam, NL, vol. 7, No. 10, May 20, 1997 (May 20, 1997), pp. 1275-1278.

Kariko et al., "Generating the optimal mRNA for therapy: HPLC purification eliminates immune activation and improves translation of nucleoside-modified, protein-encoding mRNA," Nucleic Acids Research, 2011, vol. 39, No. 21, e142, pp. 1-10.

Kariko, K., et al., "Incorporation of pseudouridine into mRNA yields superior nonimmunogenic vector with increased translational capacity and biological stability," Molecular Therapy, Nature Publishing Group, GB, vol. 16, No. 11, Nov. 1, 2008 (Nov. 1, 2008), pp. 1833-1840.

Kato, Y., et al., "New NTP analogs: the synthesis of 4'-thioUTP and 4'-thioCTP and their utility of SELEX," Nucleic Acids Research, 2005, vol. 33, No. 9, pp. 2942-2951.

Kormann, M. S. D., et al., "Expression of therapeutic proteins after delivery of chemically modified mRNA in mice," Nature Biotechnology, vol. 29, No. 2, Feb. 1, 2011 (Feb. 1, 2011), pp. 154-159.

Lehninger Principles of Biochemistry (3rd Ed.); Nelson, D. & Cox, M. (Ed.) Worth Publishers, NY, NY. Chapter 10: Nucleotides and Nucleic Acids. pp. 325-362.

La Teana et al., From stand-by to decoding site. Adjustment of the mRNA on the 30S ribosomal subunit under the influence of the initiation factors, RNA, 1:772-782 (1995).

Mauger, et al., "The genetic code as expressed through relationships between mRNA structure and protein function," FEBS Lett. vol. 587, Issue 8. Apr. 2013. pp. 1180-1188.

Minakawa, N., et al., "Investigations toward the selection of fully-modified 4'-thioRNA aptamers: Optimization of in vitro transcription steps in the presence of 4'-thioNTPs," Bioorganic & Medicinal Chemistry 16 (2008), pp. 9450-9456.

Takahashi, M., et al., "Synthesis and characterization of 2'modified-4'-thioRNA: a comprehensive comparison of nuclease stability," Nucleic Acids Research, 2009, vol. 37, No. 4, pp. 1353-1362.

Wang et al., "Systemic Delivery of Modified mRNA Encoding Herpes Simplex Virus 1 Thymidine Kinase for Targeted Cancer Gene Therapy," Molecular Therapy, 21(2): 358-367 (Feb. 2013).

Watts et al., "Chemically modified siRNA: tools and applications." Drug Discovery Today. vol. 14, Nos. 19/20. Oct. 2008. pp. 842-855.

Yamamoto, A., et al., "Current prospects for mRNA gene delivery," European Journal of Pharmaceutics and Biopharmaceutics, 71:484-489 (2009).

Lehninger et al., Principles of Biochemistry, Fifth Edition. New York, NY: W.H. Freeman and Company, Chapter 8, pp. 271-302 (2011).

\* cited by examiner

C12-200-loaded lipid nanoparticles dosing various modified and unmodified FFL mRNA in WT mice. 1.0 mg/kg dose was administered intravenously and livers were analyzed six hours post-administration.

SEQUENCE LISTING

```
<160> NUMBER OF SEQ ID NOS: 7

<210> SEQ ID NO 1
<211> LENGTH: 582
<212> TYPE: RNA
<213> ORGANISM: Artificial Sequence
<220> FEATURE:
<223> OTHER INFORMATION: chemically synthesized oligonucleotide

<400> SEQUENCE: 1 auggggugc  acgaaugucc  ugccuggcug  uggcuucucc  ugucccugcu  gucgcucccu      60
cugggccucc  caguccuggg  cgccccacca  cgccucaucu  gugacagccg  aguccuggag     120
agguaccucu  uggaggccaa  ggaggccgag  aauaucacga  cgggcugugc  ugaacacugc     180
agcuugaaug  agaauaucac  ugucccagac  accaaaguua  auuucuaugc  cuggaagagg     240
auggaggucg  ggcagcaggc  cguagaaguc  uggcagggcc  uggcccugcu  gucggaagcu     300
guccugcggg  gccaggcccu  guuggucaac  ucuucccagc  cgugggagcc  ccugcagcug     360
cauguggaua  aagccgucag  uggccuucgc  agccucacca  cucugcuucg  ggcucuggga     420
gcccagaagg  aagccaucuc  cccuccagau  gcggccucag  cugcuccacu  ccgaacaauc     480
acugcugaca  cuuuccgcaa  acucuuccga  gucuacucca  auuccuccg   gggaaagcug     540 aagcuguaca  caggggaggc  cugcaggaca  ggggacagau  ga                        582

<210> SEQ ID NO 2
<211> LENGTH: 1290
<212> TYPE: RNA
<213> ORGANISM: Artificial Sequence
<220> FEATURE:
<223> OTHER INFORMATION: chemically synthesized oligonucleotide

<400> SEQUENCE: 2
augcagcuga  ggaacccaga  acuacaucug  ggcugcgcgc  uugcgcuucg  cuuccuggcc      60
cucguuuccu  gggacaucccuggggcuaga gcacuggaca  auggauuggc  aaggacgccu     120
accaugggcu  ggcugcacug  ggagcgcuuc  augugcaacc  uugacugcca  ggaagagcca     180
gauuccugca  ucagugagaa  gcucuucaug  gagauggcag  agcucauggu  cucagaaggc    240
```

| | |
|---|---|
| uggaaggaug caggutuauga guaccucugc auugaugacu guuggauggc ucccaaaga | 300 |
| gauucagaag gcagacuuca ggcagacccu cagcgcuuuc cucaugggau ucgccagcua | 360 |
| gcuaauuaug uucacagcaa aggacugaag cuagggauuu augcagaugu uggaaauaaa | 420 |
| accugcgcag gcuucccugg gaguuuugga uacuacgaca uugaugccca gaccuuugcu | 480 |
| gacuggggag uagaucugcu aaaauuugau gguuguuacu gugacaguuu ggaaauuug | 540 |
| gcagaugguu auaagcacau guccuuggcc cugaauagga cuggcagaag cauuguguac | 600 |
| uccugugagu ggccucuuua uaugugggcc uuucaaaagc ccaauuauac agaaauccga | 660 |
| caguacugca aucacggcg aaauuuugcu gacauugaug auuccuggaa aaguauaaag | 720 |
| aguaucuugg acuggacauc uuuuaaccag gagagaauug uugauguugc uggaccaggg | 780 |
| gguuggaaug acccagauau guuagugauu ggcaacuuug gccucagcug gaaucagcaa | 840 |
| guaacucaga uggcccucug ggcuaucaug gcugucccuu auucauguc uaaugaccuc | 900 |
| cgacacauca gcccucaagc caaagcucuc cuucaggaua aggacguaau ugccaucaau | 960 |
| caggaccccu uggcaagca aggguaccag cuuagacagg gagacaacuu ugaagugugg | 1020 |
| gaacgaccuc ucucaggcuu agccuggcu guagcuauga uaaaccggca ggagauuggu | 1080 |
| ggaccucgcu cuuauaccau cgcaguugcu ucccugggua aaggaguggc cuguaauccu | 1140 |
| gccugcuuca ucacacagcu ccuccccugug aaaaggaagc uagggucua ugaauggacu | 1200 |
| ucaagguuaa gaagucacau aaauccccaca ggcacuguuu ugcuucagcu agaaaauaca | 1260 |
| augcagaugu cauuaaaaga cuuacuuuaa | 1290 |

<210> SEQ ID NO 3
<211> LENGTH: 1652
<212> TYPE: RNA
<213> ORGANISM: Artificial Sequence
<220> FEATURE:
<223> OTHER INFORMATION: chemically synthesized oligonucleotide

<400> SEQUENCE: 3

| | |
|---|---|
| auggaagaug ccaaaaacau uaagaagggc ccagcgccau ucuacccacu cgaagacggg | 60 |
| accgccggcg agcagcugca caaagccaug aagcgcuacg cccuggugcc cggcaccauc | 120 |
| gccuuuaccg acgcacauau cgaggugac auuaccuacg ccgaguacuu cgagaugagc | 180 |
| guucggcugg cagaagcuau gaagcgcuau gggcugaaua caaaccaucg gaucguggug | 240 |
| ugcagcgaga auagcuugca guucuucaug cccguguugg gugcccuguu caucggugug | 300 |
| gcuguggccc cagcuaacga caucuacaac gagcgcgagc ugcugaacag caugggcauc | 360 |
| agccagccca ccgucguauu cgugagcaag aaagggcugc aaaagauccu caacgugcaa | 420 |
| aagaagcuac cgaucauaca aaagaucauc aucauggaua gcaagaccga cuaccagggc | 480 |
| uuccaaagca uguacaccuu cgugacuucc cauuugccac ccggcuucaa cgaguacgac | 540 |
| uucgugcccg agagcuucga ccgggacaaa accaucgccc ugaucaugaa caguagugggc | 600 |
| aguaccggau ugcccaaggg cguagcccua ccgcaccgca ccgcuugugu ccgauucagu | 660 |
| caugcccgcg accccaucuu cggcaaccag aucauccccg acaccgcuau ccucagcgug | 720 |
| gugccauuuc accacggcuu cggcauguuc accacgcugg cuacuugau cugcggcuuu | 780 |
| cgggucgugc ucauguaccg cuucgaggag gagcuauucu gcgcagcuu gcaagacuau | 840 |
| aagauucaau cugcccugcu ggugcccaca cuauuuagcu ucuucgcuaa gagcacucuc | 900 |
| aucgacaagu acgaccuaag caacuugcac gagaucgcca cggcggggc ccgcucagc | 960 |
| aaggagguag gugaggccgu ggccaaacgc uuccaccuac caggcauccg ccagggcuac | 1020 |

```
ggccugacag aaacaaccag cgccauucug aucaccccg aaggggacga caagccuggc    1080
gcaguaggca aggugugcc cuucuucgag gcuaaggugg uggacuugga caccgguaag    1140 acacuggug ugaaccagcg cggcgagcug ugcguccgug gccccaugau caugagcggc    1200
uacguuaaca accccgaggc uacaaacgcu cucaucgaca aggacggcug gcugcacagc    1260
ggcgacaucg ccuacuggga cgaggacgag cacuucuuca ucguggaccg gcugaagagc    1320
cugaucaaau acaagggcua ccagguagcc ccagccgaac uggagagcau ccugcugcaa    1380
caccccaaca ucuucgacgc cggggucgcc ggccugcccg acgacgaugc cggcgagcug    1440
cccgccgcag ucgucugcu ggaacacggu aaaaccauga ccgagaagga gaucguggac    1500
uauguggcca gccagguuac aaccgccaag aagcugcgcg guguguugu guucguggac    1560 gaggugccua aggacugac cggcaaguug gacgcccgca agauccgcga gauucucauu    1620
aaggccaaga agggcggcaa gaucgccgug ua                                 1652

<210> SEQ ID NO 4
<211> LENGTH: 140
<212> TYPE: RNA
<213> ORGANISM: Artificial Sequence
<220> FEATURE:
<223> OTHER INFORMATION: chemically synthesized oligonucleotide

<400> SEQUENCE: 4
ggacagaucg ccuggagacg ccauccacgc uguuugacc uccauagaag acaccgggac      60
cgauccagcc uccgcggccg ggaacggugc auuggaacgc ggauucccg ugccaagagu    120 gacucaccgu ccuugacacg                                                140

<210> SEQ ID NO 5
<211> LENGTH: 11
<212> TYPE: RNA
<213> ORGANISM: Artificial Sequence
<220> FEATURE:
<223> OTHER INFORMATION: chemically synthesized oligonucleotide

<400> SEQUENCE: 5
gggauccuac c                                                          11

<210> SEQ ID NO 6
<211> LENGTH: 100
<212> TYPE: RNA
<213> ORGANISM: Artificial Sequence
<220> FEATURE:
<223> OTHER INFORMATION: chemically synthesized oligonucleotide

<400> SEQUENCE: 6
cggguggcau cccugugacc ccuccccagu gccucuccug gcccuggaag uugccacucc     60
agugcccacc agccuugucc uaauaaaauu aaguugcauc                          100

<210> SEQ ID NO 7
<211> LENGTH: 8
<212> TYPE: RNA
<213> ORGANISM: Artificial Sequence
<220> FEATURE:
<223> OTHER INFORMATION: chemically synthesized oligonucleotide

<400> SEQUENCE: 7 uuugaauu                                                               8
```

RIBONUCLEIC ACIDS WITH 4'-THIO-MODIFIED NUCLEOTIDES AND RELATED METHODS

RELATED APPLICATIONS

This application is a continuation of U.S. patent application Ser. No. 14/776,506, filed Sep. 14, 2015, which is the U.S. National Stage Application under 35 U.S.C. § 371 of International Application No. PCT/US2014/027422, filed Mar. 14, 2014, and claims the benefit under 35 U.S.C. § 119(e) of U.S. patent application No. 61/785,098, filed Mar. 14, 2013, each of which is incorporated herein in its entirety by reference.

SEQUENCE LISTING

The instant application contains a Sequence Listing which has been submitted electronically in ASCII format and is hereby incorporated by reference in its entirety. Said ASCII copy, created Nov. 14, 2016, is named SHR-1103US_ST25 and is 6,531 bytes in size.

BACKGROUND

The present invention relates to messenger ribonucleic acids (mRNAs) comprising 4'-thio-modified nucleotide residues, compositions comprising those mRNAs, and methods of making and using same.

Gene therapy using messenger RNA has been proposed as an approach for the treatment of a variety of diseases. The concept of introduction of messenger RNA (mRNA) as a means of protein production within a host has been reported previously. Yamamoto, A. et al. Eur. J. Pharm. 71: 484-489 (2009); Debus, H. et al. J. Control Ret. 148: 334-343 (2010). However, successful administration of mRNA for in vivo protein production typically required mRNA being packaged (such as, e.g., mRNA complexed with a polymer or lipid carrier). See, e.g., International Patent Appl. Publ. Nos. WO 2011/06810 and WO 2012/170930. Administration of unpackaged (naked) mRNA required chemically-modified nucleotides to be incorporated within an mRNA to result in a more stable and beneficial therapeutic. See, e.g., M. Kormann et al. Nature Biotech. 29: 154-159 (2011); K, Kariko, Molecular Therapy 16(11): 1833-1840 (2008).

The administration of mRNAs encoding a therapeutic protein that can be produced in vivo may provide significant advantages over administration of DNA encoding the therapeutic protein as well as direct administration of the therapeutic protein. However, while the development of therapeutic mRNAs encoding therapeutic proteins represents a promising advancement in medical therapies, the utility of such treatments can still be limited by the poor stability of mRNAs in vivo, particularly those encoding full length proteins.

In particular, poor stability of mRNAs used in gene replacement therapy can result in insufficient or less optimal production of the encoded therapeutic protein in vivo. Following the administration of an mRNA that encodes a therapeutic protein, the mRNA may undergo degradation, for example upon exposure to one or more nucleases in vivo. Ribonucleases (e.g., endoribonucleases and exoribonucleases) represent a class of nuclease enzymes that are capable of catalyzing the degradation of RNA into smaller components and thereby render the mRNA unable to produce the therapeutic protein. Nuclease enzymes (e.g., RNase) are therefore capable of shortening the circulatory half-life of, for example, synthetically or recombinantly-prepared mRNAs. Following nucleolytic degradation, an mRNA is not translated, and thus, is prevented from exerting an intended therapeutic benefit, which can significantly reduce the efficacy of the mRNA gene therapy.

SUMMARY

The present invention provides an improved modified mRNA for more stable, robust and sustained in vivo protein production. The present invention is based, in part, on the realization that the stability of mRNA used to produce therapeutic proteins in vivo can be further improved by incorporating modified ribonucleotides in which the 4' oxygen in the ribose moiety is substituted by a sulfur. Although substitution of the 4' oxygen in the ribose moiety of ribonucleotides with a sulfur has been reported previously by S. Hoshika et al. (Nuc. Ac. Res. Supp. 3: 209-210 (2003)) and M. Takahashi, M. et al. (Nuc. Ac. Res. 37: 1353-1362 (2009)), both reports involved short synthetic segments of RNA containing 4'-thio residues of at most 15 residues in length for RNA interference; short RNAs of 19-21 residues comprising 4'-thio-modified nucleotides have also been reported for RNA interference (Dande et al., J. Med. Chem. 49: 1624-1634 (2006)) and for developing aptamers (up to 59 residues in length; Hoshika et al., Nuc. Ac. Res. 32: 3815-3825(2004); Kato et al., Nuc. Ac. Res. 33: 2942-2951 (2005); Minakawa et al., Bioorg. Med. Chem. 16: 9450-9456 (2008)). These reports, however, are not predictive of the effect of incorporating 4'-thioribonucleotides into a full length mRNA (that is, an mRNA encoding a full length functional therapeutic protein and optionally containing one or more noncoding regions), which generally has a length much longer than any of the interfering RNAs or aptamers tested in the prior art and does not exist in a uniformly duplexed state and may adopt a conformation with a large non-helical and/or single-stranded component. More importantly, it was unclear if mRNAs incorporating 4'-thio-modified nucleotides could be successfully used for in vivo protein production prior to the present invention. As described herein including the examples, the present inventors have successfully synthesized full length mRNAs incorporating one or more 4'-thio-modified nucleotides (e.g., 4'-thio-ATPs, 4'-thio-UTPs, 4'-thio-GTPs, and/or 4'-thio-CTPs). Despite the concern over the length of mRNAs, the present inventors were able to synthesize full length mRNAs incorporating up to 100% 4'-thio-ATPs, 100% 4'-thio-UTPs, 100% 4'-thio-GTPs, and/or 100% 4'-thio-CTPs. As shown in the Examples, such modified mRNAs are more stable than unmodified mRNAs and surprisingly, such extensive modifications do not appear to impact the ability of modified mRNAs to be effectively translated in vivo.

Accordingly, the present invention provides mRNAs that allow better control over, for example, the stability, immunogenicity, and translational efficiency of the mRNA, and compositions comprising those mRNAs and, optionally, a carrier, as well as methods of using those mRNAs and compositions to induce expression of a therapeutic protein in viva for treatment of diseases and/or disorders.

In some embodiments, the invention provides an mRNA molecule having a coding region and optionally, one or more non-coding regions, wherein the mRNA comprises at least one nucleotide residue that incorporates a 4'-thio-substituted furanose ring. In some embodiments, a provided mRNA contains at least about 5%, 10%, 15%, 20%, 25%, 30%, 35%, 40%, 45%, 50%, 60%, 65%, 70%, 75%, 80%, 85%, 95%, 96%, 97%, 98%, or 99% nucleotide residues that incorporate a 4'-thio-substituted furanose ring. In some embodiments, a provided mRNA contains 100% nucleotide residues that incorporate a 4'-thio-substituted furanose ring. In some embodiments, a provided mRNA contains up to 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% 4'-thio-ATPs. In some embodiments, a provided mRNA contains up 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% 4'-thio-UTPs. In some embodiments, a provided snRNA contains up to 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% 4'-thio-GTPs. In some embodiments, a provided mRNA contains up to 5%, 10%, 15%, 20%, 25%, 30%, 35%, 40%, 45%, 50%, 55%, 60%, 65%, 70%. 75%, 80%, 85%, 90%, 95%, 96%, 97%, 98%, 99% or 100% 4'-thio-CTPs. In some embodiments, a provided mRNA contains a combination of various 4'-thio-modified NTPs described herein.

In some embodiments, a provided mRNA comprises a non-coding region. In some embodiments, a provided mRNA comprises a poly-A and/or a poly-U tail. In some embodiments, a provided mRNA comprises a 5' cap structure.

In some embodiments, a provided mRNA further comprises at least one nonstandard nucleotide residue. In some embodiments, the at least one nonstandard nucleotide residue is chosen from one or more of 5-methyl-cytidine, pseudouridine, and 2-thio-uridine. In some embodiments, the at least one nonstandard nucleotide residue incorporates a 4'-thio-furanose ring. In some embodiments, up to 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% nonstandard nucleotide residues incorporate a 4'-thio-furanose ring.

In some embodiments, a provided mRNA is at least 60 residues in length. In some embodiments, a provided mRNA is at least about 70, about 80, about 90, about 100, about 150, about 200, about 300, about 400, about 500, about 1,000, about 1,500, about 2,000, about 2,500, about 3,000, about 3,500, about 4,000, about 4,500, or about 5,000 residues in length.

Additional embodiments of the invention provide compositions comprising at least one mRNA molecule having a coding region and optionally, one or more non-coding regions, wherein the mRNA comprises at least one nucleotide residue that incorporates a 4'-thio-substituted furanose ring and a carrier. In some embodiments, a provided composition comprises at least one mRNA having a coding region and optionally, one or more non-coding regions, wherein the mRNA comprises at least one nucleotide residue that incorporates a 4'-thio-substituted furanose ring and a carrier, and the mRNA is at least 60 residues in length. In certain embodiments, the compositions of the invention comprise at least one mRNA molecule having a coding region and optionally, one or more non-coding regions, wherein the mRNA comprises at least one nucleotide residue that incorporates a 4'-thio-substituted furanose ring, and is complexed with a polymer based carrier or a lipid nanoparticle.

The invention further provides methods of producing a therapeutic protein in vivo, comprising administering to a subject at least one mRNA molecule having a coding region and optionally, one or more non-coding regions, wherein the mRNA comprises at least one nucleotide residue that incorporates a 4'-thio-substituted furanose ring, or a composition comprising such mRNA and a carrier. The invention also provides methods of treating a subject in need of a therapeutic protein, comprising administering at least one mRNA molecule having a coding region and optionally, a non-coding region, wherein the mRNA comprises at least one nucleotide residue that incorporates a 4'-thio-substituted furanose ring, or a composition comprising such mRNA and a carrier. In some embodiments, an administered mRNA in a provided method is at least 60 residues in length. Various modified mRNAs described herein may be used for production of therapeutic proteins or for treatment of various diseases, disorders or conditions.

In some embodiments, the present invention provides a method for producing a protein using a modified mRNA described herein. Such a method of protein production may be used in an in vitro cell free system, in vitro cell based system, or in vivo system. In various embodiments, a suitable mRNA comprises at least one nucleotide residue that incorporates a 4'-thio-substituted furanose ring. In some embodiments, a suitable mRNA comprises up to about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of nucleotide residues (e.g., ATP, CTP, GTP, UTP, and/or non-standard NTPs) that incorporate a 4'-thio-substituted furanose ring. In some embodiments, a provided mRNA comprises a poly(A) or poly(U) tail. In some embodiments, a provided mRNA is at least 60 residues in length.

In some embodiments, the present invention provides use of a provided mRNA molecule for the manufacture of a medicament that is capable of producing a therapeutic protein in vivo.

In some other embodiments, the present invention provides a method for making a provided mRNA. In some other embodiments, the present invention provides a method for in vitro synthesis of a provided mRNA. In some other embodiments, the present invention provides a method for making (e.g., in vitro synthesizing) a provided mRNA containing up to about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of nucleotide residues (e.g., ATP, CTP, GTP, UTP, and/or non-standard NTPs) that incorporate a 4'-thio-substituted furanose ring. In some embodiments, the present invention provides a method for making (e.g., in vitro synthesizing) a provided mRNA at least about 60, about 70, about 80, about 90, about 100, about 150, about 200, about 300, about 400, about 500, about 1,000, about 1,500, about 2,000, about 2,500, about 3,000, about 3,500, about 4,000, about 4,500, or about 5,000 residues in length.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed. The accompanying drawing, which is incorporated in and constitutes a part of this specification, illustrates several embodiments of the invention and together with the description, serves to further explain the principles of the invention.

BRIEF DESCRIPTION OF THE DRAWINGS

The drawings are for illustration purposes only, not for limitation.

DETAILED DESCRIPTION OF THE INVENTION

As used herein, the term "mRNA" is used to refer to modified and/or unmodified RNA including a coding region and, optionally, a noncoding region. The term "coding region" refers to a portion or region of the mRNA that can be translated into a chain of amino acids, i.e., two or more amino acids linked by peptide bonds. A chain of amino acids is also referred to as a peptide or a polypeptide, which can fold into a protein (e.g., a therapeutic protein). The term "noncoding region" refers to a portion or region of the mRNA that are typically not translated. Noncoding region typically includes 5' untranslated region and/or 3' untranslated region including but not limited to a poly(A) or poly(U) tail.

A "nonstandard nucleobase" is a base moiety other than the natural bases adenine (A), cytosine (C), guanine (G), thymine (T), or uracil (U). The nonstandard nucleobase is an analog of a specific nucleobase (A, C, G, T, or U) when its base pairing properties in a nucleic acid double helix and locus of incorporation by DNA or RNA polymerases in a nucleic acid double helix (including a local RNA-DNA helix such as that formed during transcription of a DNA template by RNA polymerase) are most similar to one of the five previously listed nucleobases, with the exception that analogs of T will generally also be analogs of U and vice versa. The term "nonstandard" used in conjunction with terms including but not limited to "nucleoside," "base," "nucleotide," or "residue" is to be interpreted in the same manner as if it were used in conjunction with "nucleobase."

As used herein, the term "therapeutic protein" includes any protein that, if administered to a subject, provides a beneficial effect on the health and well-being of the subject. In some embodiments, a deficiency, lack of or aberrant expression of that protein in a subject gives rise to a disease or condition. "Therapeutic protein" may also refer to a protein that is not normally present or is not normally present in sufficient quantities in a subject to achieve a desired therapeutic effect.

The term "helper lipid" as used herein refers to any neutral or zwitterionic lipid material including cholesterol. Without wishing to be held to a particular theory, helper lipids may add stability, rigidity, and/or fluidity within lipid bilayers/nanoparticles.

Figure 1:
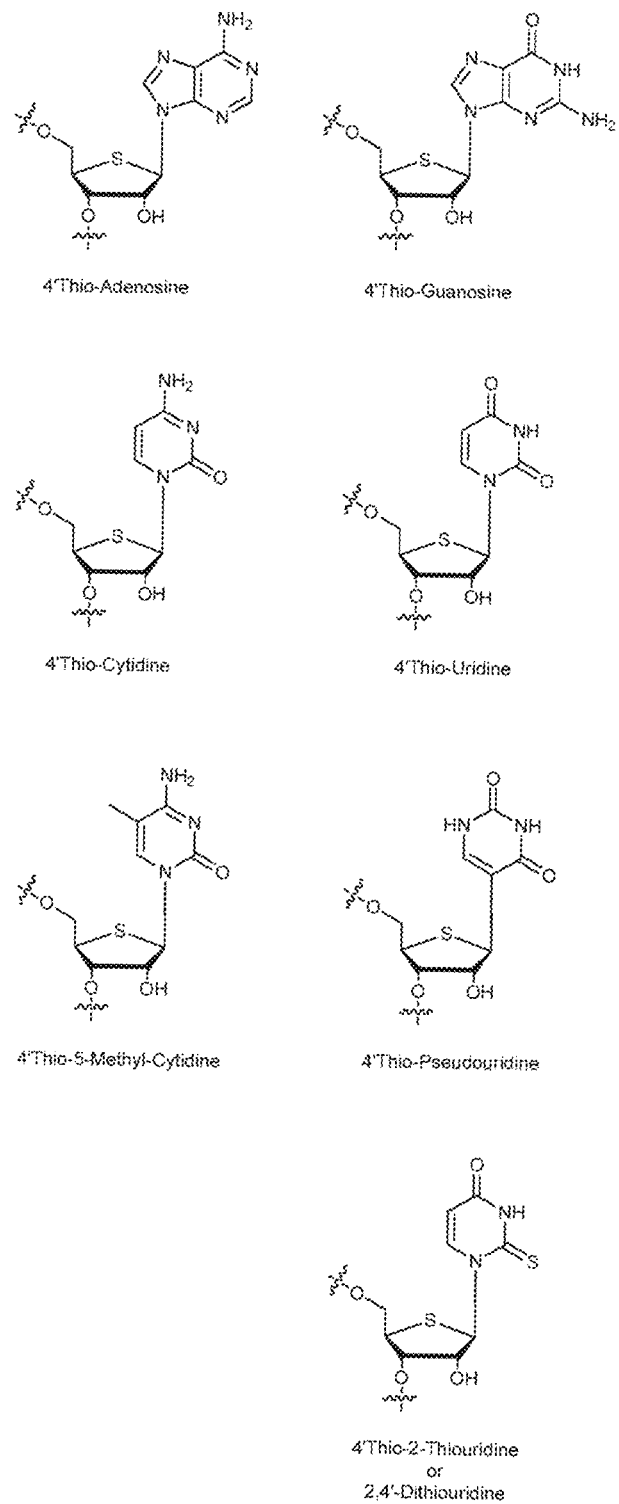
FIG. 1 shows molecular structures of exemplary 4'-thio-RNA bases: 4'-thio-adenosine, 4'-thio-guanosine, 4'-thio-cytidine, 4'-thio-uridine, 4'-thio-5-methyl-cytidine, 4'-thio-pseudouridine, and 4'-thio-2-thiouridine.

The mRNAs of the invention employ specific chemically-modified bases, in which the 4' oxygen in the ribose moiety of a nucleotide residue is replaced with sulfur, for substitution into a messenger ribonucleic acid molecule to enhance its biological properties upon administration to a subject. Exemplary 4'-thio modified nucleotide residues for incorporation into an mRNA of the invention are depicted in FIG. 1 (showing modified nucleotide residues containing a thio-substituted furanose ring). In some embodiments, 4'-thio modification of the furanose ring provides improved resistance to exonucleases, endonucleases, and/or other RNA degradation enzymes in human serum. Such stability can afford an increased RNA half-life. Thus, for example, administration of an mRNA having a 4'-thio modification in the furanose ring or a composition comprising such mRNA results in cellular uptake of an mRNA having improved biological properties, e.g., increased half-life, which in turn contributes to increased protein production in vivo.

In certain embodiments, at least 1% of the adenosine nucleotide residues in the RNA have a 4'-thio modification in the furanose ring. For example, about 1-5%, 5-15%, 15-30%, 30-50%, 50-75%, 75-90%, 90-99%, or 99-100% of the adenosine in the mRNA can be 4'-thio-adenosine.

In some embodiments, at least about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98% or about 99% of the adenosine residues in the mRNA are 4'-thio-adenosine. In some embodiments, about 100% of the adenosine residues in the mRNA are 4'-thio-adenosine.

In certain embodiments, at least 1% of the guanosine nucleotide residues in the RNA have a 4'-thio modification in the furanose ring. For example, about 1-5%, 5-15%, 15-30%, 30-50%, 50-75%, 75-90%, 90-99%, or 99-100% of the guanosine in the mRNA can be 4'-thio-guanosine.

In some embodiments, at least about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98% or about 99% of the guanosine residues in the mRNA are 4'-thio-guanosine. In some embodiments, about 100% of the guanosine residues in the mRNA are 4'-thio-guanosine.

In certain embodiments, at least 1% of the uridine nucleotide residues in the RNA have a 4'-thio modification in the furanose ring. For example, about 1-5%, 5-15%, 15-30%, 30-50%, 50-75%, 75-90%, 90-99%, or 99-100% of the uridine in the mRNA can be 4'-thio-uridine.

In some embodiments, at least about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98% or about 99% of the uridine residues in the mRNA are 4'-thio-uridine. In some embodiments, about 100% of the uridine residues in the mRNA are 4'-thio-uridine.

In certain embodiments, at least 1% of the cytidine nucleotide residues in the RNA have a 4'-thio modification in the furanose ring. For example, about 1-5%, 5-15%, 15-30%, 30-50%, 50-75%, 75-90%, 90-99%, or 99-100% of the cytidine in the mRNA can be 4'-thio-cytidine.

In some embodiments, at least about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98% or about 99% of the cytidine residues in the mRNA are 4'-thio-cytidine. In some embodiments, about 100% of the cytidine residues in the mRNA are 4'-thio-cytidine.

In some embodiments, each 4'-thio-modified nucleotide in a provided mRNA is 4'-thio-uridine. In some embodiments, each 4'-thio-modified nucleotide in a provided mRNA is 4'-thio-cytidine. In some embodiments, each 4'-thio-modified nucleotide in a provided snRNA is independently 4'-thio-uridine or 4'-thio-cytidine. In some embodiments, a provided mRNA comprises at least 5, 10, 15, 20, 25, 30, 35, 40, 45, 50, 55, 60, 65, 70, 75, 80, 85, 90, 95, 100 or more 4'-thio-uridine or 4'-thio-cytidine. In some embodiments, a provided mRNA comprises at least one 4'-thio-adenosine residue. In some embodiments, a provided mRNA comprises at least one 4'-thio-guanosine residue. In some embodiments, a provided mRNA comprises at least one 4'-thio-guanosine, or 4'-thio-adenosine residue. In some embodiments, a provided mRNA comprises at least 5, 10, 15, 20, 25, 30, 35, 40, 45, 50, 55, 60, 65, 70, 75, 80, 85, 90, 95, 100 or more 4'-thio-guanosine or 4'-thio-adenosine residues.

In certain embodiments, the fraction of nucleotide residues with a 4'-thio modification in the furanose ring of one base type (e.g., adenosine, guanosine, uridine, or cytidine) varies independently of the fraction of modified nucleotide residues of the other base types.

In certain embodiments, less than 10% of the nucleotide residues have a 4'-thio modification in the furanose ring. For example, about 1-5%, 5-10%, 3-5%, 1-3%, 0.1-1%, or 0.01-0.1% of the nucleotide residues can incorporate a 4'-thio-substituted furanose ring.

In other embodiments, more than 10% of the nucleotide residues have a 4'-thio modification in the furanose ring. For example, about 10-15%, 15-20%, 20-25%, 25-30%, 30-35%, 35-40%, 40-45% or 45-50% of the nucleotide residues can incorporate a 4'-thio-substituted furanose ring. In some embodiments, more than 50% of the nucleotide residues have a 4'-thioRNA modification in the furanose ring. For example, about 50-55%, 55-60%, 60-65%, 65-70%, 70-75%, 75-80%, 80-85%, 85-90%, 90-95%, 95-100%, 95-97%, 97-98%, 98-99%, 99-99.9%, or 99.9-100% of the nucleotide residues incorporate a 4'-thio-substituted furanose ring.

In some embodiments, at least about 1%, 5%, 10%, 15%, 20%, 25%, 30%, 35%, 40% 45%, 50% 55%, 60% 65%, 70%, 75%, 80%, 85%, 90%, 95%, 96%, 97%, 98%, or 99% of the nucleotide residues can incorporate a 4'-thio-substituted furanose ring. In some embodiments, about 100% nucleotide residues can incorporate a 4'-thio-substituted furanose ring.

The coding and non-coding regions in the mRNAs of the invention may encompass non-contiguous regions of sequence. The optional non-coding regions may include one or more of a 5' untranslated region (UTR), a 3' UTR, a poly-A, poly-U or poly-C tail, and/or a 5' cap structure. In some embodiments, a provided mRNA comprises a non-coding region. In some embodiments, a provided mRNA comprises a 5' UTR. In some embodiments, a provided mRNA comprises a 3' UTR. In some embodiments, a provided mRNA comprises a 5' cap structure. In some embodiments, a provided mRNA comprises a poly-A tail. In some embodiments, a provided mRNA comprises a 5'-UTR sequence, a 3'-UTR sequence and a poly-A tail. In some embodiments, a provided mRNA comprises a 5'-UTR sequence, a coding region, a 3'-UTR sequence and a poly-A tail. In some embodiments, a provided mRNA comprises a 5'-UTR sequence, a 5' cap, a 3'-UTR sequence and a poly-A tail. In some embodiments, a provided mRNA comprises a 5'-UTR sequence, a 5' cap, a coding region, a 3'-UTR sequence and a poly-A tail.

In certain embodiments, the poly-A, poly-U or poly-C tail comprises nucleotide residues that incorporate a 4'-thio-substituted furanose ring. In some embodiments, only the poly-A, poly-U or poly-C tail or other components of the non-coding region incorporate nucleotide residues having a 4'-thio substitution in the furanose ring, while the remainder of the nucleotide residues in the mRNA molecule do not contain a 4'-thio-furanose modification. In some embodiments, the coding region comprises nucleotide residues that incorporate a 4'-thio-substituted furanose ring. In certain embodiments, both the coding and non-coding regions (if present) incorporate nucleotide residues having a 4'-thio substitution in the furanose ring. In certain embodiments, the length of the poly-A, poly-U or poly-C tail may vary. For example, the length of the poly-A, poly-U, or poly-C tail may be at least about 50, 70, 90, 100, 150, 200, 250, 300, 400, or 500 nucleotides in length. In some embodiments, the length of the poly-A, poly-U or poly-C tail is less than about 90, 100, 150, 200, 250, 300, 400, or 500 nucleotides in length. In certain embodiments, the mRNA molecule may include modifications in addition to a 4'-thio-substituted furanose ring. For example, the molecule may incorporate any nonstandard nucleobase. Certain embodiments may include nucleotide residue modifications such as 5-methyl-cytidine ("5mC"), pseudouridine ("ψU"), 2-thio-uridine ("2sU"), 5-methylcytosine, isocytosine, pseudoisocytosine, 5-bromouracil, 5-propynyluracil, 6-aminopurine, 2-aminopurine, inosine, diaminopurine and 2-chloro-6-aminopurine cytosine as well as combinations of these modifications and other nucleotide residue modifications. Certain embodiments may further include additional modifications to the furanose ring or other parts of the nucleotide residue, e.g., the nucleobase. For example, in some embodiments, a 4'-thio substituted furanose ring can be included within an unmodified or a modified base such as, e.g., pseudouridine, 2-thiouridine, and 5-methylcytidine. In certain embodiments, any of these modifications may be present in 0-100% of the nucleotide residues for example, more than 0%, 1%, 10%, 50%, 90% or 95%, or 100% of the nucleotide residues individually or in combination. In some embodiments, a provided mRNA comprises at least one nonstandard nucleotide residue. In some embodiments, the at least one nonstandard nucleotide residue is chosen from one or more of 5-methyl-cytidine, pseudouridine, and 2-thio-uridine. In some embodiments, the at least one nonstandard nucleotide residue in 5-methyl-cytidine. In some embodiments, the at least one nonstandard nucleotide residue incorporates a 4'-thio-furanose ring. In some embodiments, up to 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% nonstandard nucleotide residues incorporate a 4'-thio-furanose ring.

Additional modifications may include, for example, sugar modifications or substitutions (e.g., one or more of a 2'-O-alkyl modification, a locked nucleic acid (LNA)). In embodiments where the sugar modification is a 2'-O-alkyl modification, such modification may include, but are not limited to a 2"-deoxy-2'-fluoro modification, a 2'-O-methyl modification, a 2'-O-methoxyethyl modification and a 2'-deoxy modification.

In certain embodiments, 0-100% of the mRNA may be single-stranded. In certain embodiments, 0-100% of the RNA may adopt a non-helical conformation.

In certain embodiments, the compositions of the invention comprise mRNAs in which about 100% of the uridine residues are replaced with 4'-thio-uridine.

In certain embodiments, the compositions of the invention comprise mRNAs in which about 100% of the uridine residues are replaced with 4'-thio-uridine and about 100% of the cytidine residues are replaced with 5-methyl-cytidine.

In certain embodiments, the compositions of the invention comprise mRNAs in which about 100% of the uridine residues are replaced with 4'-thio-pseudouridine.

In certain embodiments, the compositions of the invention comprise mRNAs in which about 100% of the uridine residues are replaced with 4'-thio-pseudouridine and about 100% of the cytidine residues are replaced with 5-methyl-cytidine.

In some embodiments, a provided mRNA provides a beneficial biological effect, for example but not limited to increased stability, improved protein production rate, and/or higher protein yield, when compared with a corresponding natural mRNA. In some embodiments, a provided mRNA has increased stability (e.g., a longer serum half-life) when administered in vivo, as compared with a corresponding natural mRNA (i.e., a corresponding mRNA without modification).

The mRNA of the invention can be more resistant to nuclease (e.g., endonuclease) degradation to an extent that results in an increase in the amount of the therapeutic protein translated from the mRNA transcript upon administration to a subject by at least about 2.5%, 5%, 7.5%, 10%, 15%, 20%, 25%, 30%, 33%, 36%, 40%, 50%, 60%, 70%, 75%, 80%, 90%, 95%, 99%, 100%, 110%, 120%, 125%, 150%, 175%, 200%, 250%, 300%, 400%, 500%, 600%, 700%, 750%, 800%, 900%, or 1,000%, as compared to a corresponding mRNA without modification.

In certain embodiments, the length of the modified mRNA molecule in the compositions of the invention is at least 200 nucleotide residues in length. For example, the mRNA may be at least about 200, 300, 400, 500, 1000, 2000, 3000, 4000, or 5000 nucleotide residues in length. In some embodiments, a provided mRNA is at least 60 residues in length. In some embodiments, a provided mRNA is at least about 70, about 80, about 90, about 100, about 150, about 200, about 300, about 400, about 500, about 600, about 700, about 800, about 900, about 1,000, about 1,500, about 2,000, about 2,500, about 3,000, about 4,000, about 5,000, about 6,000 or about 7000 residues in length.

In some embodiments of the invention, the therapeutic protein encoded by the mRNAs of the invention may be any protein where a deficiency, lack of, or aberrant expression of that protein gives rise to a disease and/or condition. In some embodiments, the therapeutic protein may be an enzyme. In other embodiments, the therapeutic protein is one that is not normally present or is not normally present in sufficient quantities in a subject to achieve the desired therapeutic effect.

For example, a non-limiting selection of suitable therapeutic proteins includes erythropoietin, insulin, human growth hormone, cystic fibrosis transmembrane conductance regulator (CFTR), insulin, alpha-galactosidase A, alpha-L-iduronidase, iduronate-2-sulfatase, N-acctyloglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), arginase 1 (ARG1), glucose-6-phosphatase, glucose-6-phosphate translocase, glycogen debranching enzyme, lysosomal alpha-glucosidase, 1,4-alpha-glucan branching enzyme, glycogen phosphorylase, phosphofructokinase, liver phosphorylase, GLUT-2, UDP glycogen synthase, alpha-L-iduronidase, iduronate sulfate silfatase, heparan sulfate sulfamidase, alpha-N-acetylglucose amidase, alpha-glucosaminid-N-acetyltransferase, N-acetylglucosamine-6-sulfate sulfatase, apolipoprotein E, low density lipoprotein receptor (LDLR), clotting factors, such as, e.g., Factor VIII, and Factor IX, spinal motor neuron 1 (SMN1), phenylalanine hydroxylase, propionyl-CoA carboxylase, porphobilinogen deaminase, methylmalonyl-CoA mutase, urate oxidase, C1 esterase inhibitor, and acid alpha-glucosidase.

In certain embodiments, the snRNA molecules of the invention may be administered as naked or unpackaged mRNA. In some embodiments, the administration of the mRNA in the compositions of the invention may be facilitated by inclusion of a suitable carrier. In certain embodiments, the carrier is selected based upon its ability to facilitate the transfection of a target cell with one or more mRNAs.

As used herein, the term "carrier" includes any of the standard pharmaceutical carriers, vehicles, diluents, excipients and the like which are generally intended for use in connection with the administration of biologically active agents, including mRNA. The compositions and, in particular, the carriers described herein are capable of delivering and/or stabilizing mRNA of varying sizes to their target cells or tissues. In certain embodiments, the compositions of the invention comprise carriers that are capable of delivering large mRNAs mRNAs of at least 5 kDa, 10 kDa, 12 kDa, 15 kDa, 20 kDa, 25 kDa, 30 kDa, or more, or of at least 60, 70, 80, 90, 100, 150, 200, 300, 400, 500, 600, 700, 800, 900, 1,000, 1,500, 2,000, 2,500, 3,000, 3,500, 4,000, 4,500, 5,000, 5,500, 6,000, 6,500, or 7,000 residues in length). mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates including desired amount(s) of 4'-thio-modified standard and/or non-standard ribonucleotides (e.g., one or more desired 4'-thio-NTP(s)) and optionally, mixed with unmodified ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application. It is observed that 4'-thio-modified standard and/or non-standard ribonucleotides may be effectively incorporated into a full length mRNA of any length.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for encoding a protein of interest and a termination signal. Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs according to the present invention include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, mRNAs according to the present invention include a 3' tail structure. A suitable 3' tail structure includes, but is not limited to, a poly-A, poly-U and/or poly-C tail. Exemplary suitable poly-A, poly-U and poly-C tails are described above. The poly-U or poly-C tail may be added to the poly-A tail or may substitute the poly-A tail.

In some embodiments, mRNAs according to the present invention include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length (e.g., about 50 and 400 nucleotides in length, about 50 and 300 nucleotides in length, about 50 and 200 nucleotides in length, or about 50 and 100 nucleotides in length).

In certain embodiments of the present invention, the carrier may be selected and/or prepared to optimize delivery of the mRNA to a target cell, tissue or organ. For example, if the target cell is a pneumocyte the properties of the carrier (e.g., size, charge and/or pH) may be optimized to effectively deliver such carrier to the target cell or organ, reduce immune clearance, and; promote retention in that target organ. Alternatively, if the target tissue is the central nervous system (e.g., to facilitate delivery of mRNA polynucleotides to targeted brain regions) or spinal tissue) selection and preparation of the carrier must consider penetration of, and retention within, the blood brain barrier and/or the use of alternate means of directly delivering such carrier to such target tissue. In certain embodiments, the compositions of the present invention may be combined with agents that facilitate the transfer of exogenous polynucleotides from the local tissues or organs into which such compositions were administered to one or more peripheral target organs or tissues.

In certain embodiments, the carriers employed in the compositions of the invention may comprise a liposomal vesicle, or other means to facilitate the transfer of an mRNA to target cells and tissues. Suitable carriers include, but are not limited to, polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, sol-gels, calcium phosphate nanoparticulates, silicon dioxide nanoparticulates, nanocrystal line particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated is the use of bionanocapsules and other viral capsid proteins assemblies as suitable carriers. (Hum. Gene Ther. 19(9): 887-95 (2008)).

In certain embodiments of the invention, the carrier is formulated using a polymer as a carrier, alone or in combination with other carriers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PEGylated PLL and polyethylenimine (PEI), including, but not limited to branched PEI (25 kDa). In some embodiments, a polymer may be one or more multi-domain-block polymers. In some embodiments, a polymer may comprise a dry powder formulation of the polymer or polymers.

The use of liposomal carriers to facilitate the delivery of polynucleotides to target cells is also contemplated by the present invention. Liposomes (e.g., liposomal lipid nanoparticles) are generally useful in a variety of applications in research, industry, and medicine, particularly for their use as carriers of diagnostic or therapeutic compounds in vivo (Lasic et al., Trends Biotechnol., 16: 307-321 (1998); Drummond et al., Pharmacol. Rev., 51: 691-743 (1999)) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains. Bilayer membranes of the liposomes can also be termed by amphiphilic polymers and surfactants (e.g., polymerosomes, niosomes, etc.).

In certain embodiments, the mRNA molecules is complexed with lipid nanoparticles to facilitate delivery to the target cell. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). In certain embodiments, the mRNA molecules and compositions of the invention may be combined with a multi-component lipid mixture of varying ratios employing one or more cationic lipids, helper lipids and PEGylated lipids designed to encapsulate various nucleic acid-based materials.

Cationic lipids may include, but are not limited to DOTAP (1,2-dioleyl-3-trimethylammonium propane), DODAP (1,2-diolcyl-3-dimethylammonium propane), cKK-E12 (3,6-bis (4-(bis(2-hydroxydodecyl)amino)butyl)piperazine-2,5-dione), dialkylamino-based, imidazole-based, guanidinium-based, XTC (2,2-Dilinoleyl-4-dimethylaminoethyl-[1,3]-dioxolane), MC3 ((((6Z,9Z,28Z,31Z)-heptatriaconta-6,9,28, 31-tetraen-19-yl 4-(dimethylamino)butanoate), ALNY-100 ((3aR,5s,6aS)-N,N-dimethyl-2,2-di((9Z,12Z)-octadeca-9, 12-dienyl)tetrahydro-3aH-cyclopenta[d] [1,3]dioxol-5-amine)), NC98-5 (4,7,13-tris(3-oxo-3-(undecylamino)propyl)-N1, N16-diundecyl-4,7,10,13-tetraazahexadecane-1, 16-diamide), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, et al., J. Contr. Rel. 107: 276-287(2005)), DLin-KC2-DMA (Semple, et al., Nature Biotech. 28: 172-176 (2010)), C12-200 (Love, et al., Proc. Nat'l. Acad., Sci. 107: 1864-1869(2010)). In some embodiments, a cationic lipid is cKK-E12:

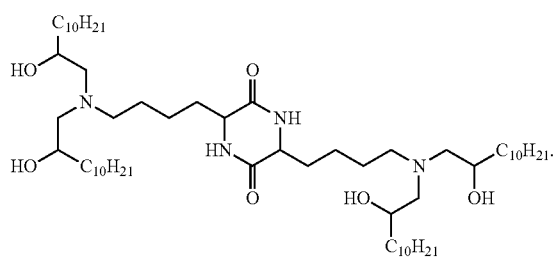

Suitable helper lipids include, but are not limited to DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-sn-glycero-3-phospho-(1'-rac-glycerol)), and cholesterol.

PEGylated lipids for use in nanoparticle formulations include, but are not limited to a poly(ethylene) glycol chain of up to 5 kDa in length covalently attached to a lipid with alkyl chain(s) of C6-C20 length, DMG-PEG2K, PEG-DSG, PEG-DMG, and PEG-ceramides.

In certain embodiments, the lipid nanoparticle carrier comprises one of the following lipid formulations:
C12-200, DOPE, cholesterol, DMG-PEG2K;
DODAP, DOPE, cholesterol, DMG-PEG2K;
HGT5000, DOPE, cholesterol, DMG-PEG2K;
HGT5001, DOPE, cholesterol, DMG-PEG2K;
XTC, DSPC, cholesterol, PEG-DMG;
MC3, DSPC, cholesterol, PEG-DMG;
ALNY-100, DSPC, cholesterol, PEG-DSG.

In certain embodiments, the mRNAs of the invention and compositions comprising those mRNAs may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing the mRNAs and compositions of the invention can be inhaled (for nasal, tracheal, or bronchial delivery); mRNAs and compositions of the invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form tier rectal or vaginal application; or can even be delivered to the eye by use of creams, drops, or even injection.

Also contemplated herein are lyophilized pharmaceutical compositions comprising one or more of the liposomal nanoparticles disclosed herein and related methods for the use of such lyophilized compositions as disclosed for example, in International Patent Publication WO 2012/170889, the teachings of which are incorporated herein by reference in their entirety. For example, lyophilized mRNA and compositions of the invention may be reconstituted prior to administration or can be reconstituted in vivo. For example, a lyophilized mRNA and/or composition can be formulated in an appropriate dosage form (e.g., an intradermal dosage form such as a disk, rod or membrane) and administered such that the dosage form is rehydrated over time in vivo by the individual's bodily fluids.

In certain embodiments, methods of treating a subject comprising administering an mRNA or composition of the invention are also contemplated. For example, certain embodiments of the invention provide methods of treating or preventing conditions in which production of a particular protein and/or utilization of a particular protein is inadequate or compromised. In some embodiments, the present invention provides methods of modulating (e.g., increasing, improving or otherwise enhancing) the translational efficiency of one or more mRNAs in a target cell. As used herein, the phrase "translational efficiency" refers to the extent to which an mRNA is translated and the encoded therapeutic protein is produced.

In certain embodiments, an mRNA molecule of the invention or composition comprising such mRNA is administered to a patient.

In some embodiments, an mRNA molecule of the invention or composition comprising such mRNA is used for protein production in an in vitro or in vivo system. A suitable in vitro system my be an in vitro cell free system or an in vitro cell based system. A suitable in vivo system may be any living organism such as a non-human animal (e.g., rat, mouse, pig, dog, chicken, sheep, non-human primate, etc.) or human.

EXAMPLES

The following specific examples are to be construed as merely illustrative, and not limiting of the scope of the disclosure. Without further elaboration, it is believed that one skilled in the art can, based on the description herein, utilize the present invention to its fullest extent.

Example 1

Synthesis and Expression of mRNA Incorporating 4'-Thio-Substituted Furanose Ring Art mRNA which encodes a protein is synthesized. The mRNA contains at least one 4'-thio-substituted furanose ring. The mRNA is formulated into a pharmaceutical composition and administered to a subject. The mRNA may exhibit a longer half-life and result in a greater amount of synthesis of the protein encoded by the mRNA than a control mRNA which does not contain a 4'-thio-substituted furanose ring.

I. Formulation Experimental Details

I-a. Messenger RNA Material

Firefly Luciferase (FFL), human erythropoietin (EPO) and human alpha-galactosidase (GLA) are synthesized by in vitro transcription from a plasmid DNA template encoding the gene, which is followed by the addition of a 5' cap structure (Cap1) (Fechter and Brownlee, J. Gen. Virology 86: 1239-1249(2005)) and a 3' poly(A) tail of approximately 200 nucleotides in length as determined by gel electrophoresis. 5' and 3' untranslated regions present in each snRNA product are represented as X and Y, respectively and defined as stated (vide infra).

Human erythropoietin (EPO) mRNA (SEQ ID NO: 1):
X₁AUGGGGGUGCACGAAUGUCCUGCCUGGCUGUGGCUUCUCCUGUCCCUG

CUGUCGCUCCCUCUGGGCCUCCCAGUCCUGGGCGCCCCACCACGCCUCAU

CUGUGACAGCCGAGUCCUGGAGAGGUACCUCUUGGAGGCCAAGGAGGCCG

AGAAUAUGACGACGGGCUGUGCUGAACACUGCAGCUUGAAUGAGAAUAUC
ACUGUCCCAGACACCAAAGUUAAUUUCUAUGCCUGGAAGAGGAUGGAGGU
CGGGCAGCAGGCCGUAGAAGUCUGGCAGGGCCUGGCCCUGCUGUCGGAAG
CUGUCCUGCGGGGCCAGGCCCUGUUGGUCAACUCUUCCCAGCCGUGGGAG
CCCCUGCAGCUGCAUGUGGAUAAAGCCGUCAGUGGCCUUCGCAGCCUCAC
CACUCUGCUUCGGGCUCUGGGAGCCCAGAAGGAAGCCAUCUCCCCUCCAG
AUGGGGCCUCAGCUGCUCCACUCCGAACAAUCACUGCUGACACUUUCCGC
AAACUCUUCCGAGUCUACUCCAAUUUCCUCCGGGGAAAGCUGAAGCUGUA
CACAGGGGAGGCCUGCAGGACAGGGGACAGAUGAY$_1$

Human alpha-galactosidase (GLA) mRNA (SEQ ID NO: 2):
X$_1$AUGCAGCUGAGGAACCCAGAACUACAUCUGGGCUGCGCGCUUGCGCUU
CGCUUCCUGGCCCUCGUUUCCUGGGACAUCCCUGGGGCUAGAGCACUGGA
CAAUGGAUUGGCAAGGACGCCUACCAUGGGCUGGCUGCACUGGGAGCGCU
UCAUGUGCAACCUUGACUGCCAGGAAGAGCCAGAUUCCUGCAUCAGUGAG
AAGCUCUUCAUGGAGAUGGCAGAGCUCAUGGUCUCAGAAGGCUGGAAGGA
UGCAGGUUAUGAGUACCUCUGCAUUGAUGACUGUUGGAUGGCUCCCCAAA
GAGAUUCAGAAGGCAGACUUCAGGCAGACCCUCAGCGCUUUCCUCAUGGG
AUUCGCCAGCUAGCUAAUUAUGUUCACAGCAAAGGACUGAAGCUAGGGAU
UUAUGCAGAUGUUGGAAAUAAAACCUGCGCAGGCUUCCCUGGGAGUUUUG
GAUACUACGACAUUGAUGCCCAGACCUUUGCUGACUGGGGAGUAGAUCUG
CUAAAAUUUGAUGGUUGUUACUGUGACAGUUUGGAAAAUUUGGCAGAUGG
UUAUAAGCACAUGUCCUUGGCCCUGAAUAGGACUGGCAGAAGCAUUGUGU
ACUCCUGUGAGUGGCCUCUUUAUAUGUGGCCCUUUCAAAAGCCCAAUUAU
ACAGAAAUCCGACAGUACUGCAAUCACUGGCGAAAUUUUGCUGACAUUGA
UGAUUCCUGGAAAAGUAUAAAGAGUAUCUGGACUGGACAUCUUUUAACC
AGGAGAGAAUUGUUGAUGUUGCUGGACCAGGGGGUUGGAAUGACCCAGAU
AUGUUAGUGAUUGGCAACUUUGGCCUCAGCUGGAAUCAGCAAGUAACUCA
GAUGGCCCUCUGGGCUAUCAUGGCUGCUCCUUUAUUCAUGUCUAAUGACC
UCCGACACAUCAGCCCUCAAGCAAAGCUCUCCUUCAGGAUAAGGACGUA
AUUGCCAUCAAUCAGGACCCCUUGGGCAAGCAAGGGUACCAGCUUAGACA
GGGAGACAACUUUGAAGUGUGGGAACGACCUCUCUCAGGCUUAGCCUGGG
CUGUAGCUAUGAUAAACCGGCAGGAGAUUGGUGGACCUCGCUCUUUAUACC
AUCGCAGUUGCUUCCCUGGGUAAAGGAGUGGCCUGUAAUCCUGCCUGCUU
CAUCACACAGGUCCUCCCUGUGAAAAGGAAGCUAGGGUUCUAUGAAUGGA
CUUCAAGGUUAAGAAGUCACAUAAAAUCCCACAGGCACUGUUUUGCUUCAG
CUAGAAAAUACAAUGCAGAUGUCAUUAAAAGACUUACUUUAAY$_1$ Codon-Optimized Firefly Luciferase (FFL) mRNA (SEQ ID NO: 3):
X$_2$AUGGAAGAUGCCAAAAACAUUAAGAAGGGCCCAGCGCCAUUCUACCCA
CUCGAAGACGGGACCGCCGGCGAGCAGCUGCACAAAGCCAUGAAGCGCUA
CGCCCUGGUGCCCGGCACCAUCGCCUUUACCGACGCACAUAUCGAGGUGG ACAUUACCUACGCCGAGUACUUCGAGAUGAGCGUUCGGCUGGCAGAAGCU
AUGAAGCGCUAUGGGCUGAAUACAAACCAUCGGAUCGUGGUGUGCAGCGA
GAAUAGCUUGCAGUUCUUCAUGCCCGUGUUGGGUGCCCUGUUCAUCGGUG
UGGCUGUGGCCCCAGCUAACGACAUCUACAACGAGCGCGAGCUGCUGAAC
AGCAUGGGCAUCAGCCAGCCCACCGUCGUAUUCGUGAGCAAGAAAGGGCU
GCAAAAGAUCCUCAACGUGCAAAAGAAGCUACCGAUCAUACAAAAGAUCA
UCAUCAUGGAUAGCAAGACCGACUACCAGGGCUUCCAAAGCAUGUACACC
UUCGUGACUUCCCAUUUGCCACCCGGCUUCAACGAGUACGACUUCGUGCC
CGAGAGCUUCGACCGGGACAAAACCAUCGCCCUGAUCAUGAACAGUAGUG
GCAGUACCGGAUUGCCCAAGGGCGUAGCCCUACCGCACCGCACCGCUUGU
GUCCGAUUCAGUCAUGCCCGCGACCCCAUCUUCGGCAACCAGAUCAUCCC
CGACACCGCUAUCCUCAGCGUGGUGCCAUUUCACCACGGCUUCGGCAUGU
UCACCACGCUGGGCUACUUGAUCCGCGGCUUUCGGGUCGUGCUCAUGUAC
CGCUUCGAGGAGGAGCUAUUCUUGCGCAGCUUGCAAGACUAUAAGAUUCA
AUCUGCCCUGCUGGUGCCCACACUAUUUAGCUUCUUCGCUAAGAGCACUC
UCAUCGACAAGUACGACCUAAGCAACUUGCACGAGAUCGCCAGCGGCGGG
GCGCCGCUCAGCAAGGAGGUAGGUGAGGCCGUGGCCAAACGCUUCCACCU
ACCAGGCAUCCGCCAGGGCUACGGCCUGACAGAAACAACCAGCGCCAUUC
UGAUCACCCCCGAAGGGGACGACAAGCCUGGCGCAGUAGGCAAGGUGGUG
CCCUUCUUCGAGGCUAAGGUGGUGGACUUGGACACCGGUAAGACACUGGG
UGUGAACCAGCGCGGCGAGCUGUGCGUCCGUGGCCCCAUGAUCAUGAGCG
GCUACGUUAACAACCCCGAGGCUACAAACGCUCUCAUCGACAAGGACGGC
UGGCUGCACAGCGGCGACAUCGCCUACUGGGACGAGGACGAGCACUUCUU
CAUCGUGGACCGGCUGAAGAGCCUGAUCAAAUACAAGGGCUACCAGGUAG
CCCCAGCCGAACUGGAGAGCAUCCUGCUGCAACACCCCAACAUCUUCGAC
GCCGGGGUCGCCGGCCUGCCCGACGACGAUGCCGGCGAGCUGCCCGCCGC
AGUCGUCGUGCUGGAACACGGUAAAACCAUGACCGAGAAGGAGAUCGUGG
ACUAUGUGGCCAGCCAGGUUACAACCGCCAAGAAGCUGCGCGGUGGUGUU
GUGUUCGUGGACGAGGUGCCUAAAGGACUGACCGGCAAGUUGGACGCCCG
CAAGAUCCGCGAGAUUCUCAUUAAGGCCAAGAAGGGCGGCAAGAUCGCCG
UGUAY$_2$ X$_1$ (5′ untranslated sequence) (SEQ ID NO: 4):
GGACAGAUCGCCUGGAGACGCCAUCCACGCUGUUUUGACCUCCAUGAAG
ACACCGGGACCGAUCCAGCCUCCGCGGCCGGGAACGGUGCAUUGGAACGC
GGAUUCCCCGUGCCAAGAGUGACUCACCGUCCUUGACACG X$_2$ (5′ untranslated sequence) (SEQ ID NO: 5):
GGGAUCCUACC -continued Y₁ (3' untranslated sequence) (SEQ ID NO: 6):
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

Y₂ (3' untranslated sequence) (SEQ ID NO: 7):
UUUGAAUU

I-b. Formulation Protocols

Protocol A: Aliquots of 50 mg/mL ethanolic solutions of C12-200, DOPE, Chol and DMG-PEG2K are mixed and diluted with ethanol to 3 mL final volume. Separately, an aqueous buffered solution (10 mM citrate/150 mM NaCl, pH 4.5) of GLA mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. Final concentration=0.85 mg/mL GLA mRNA (encapsulated). Zave=81.2 nm (Dv(50)=63.2 nm; Dv(90)=104 nm).

Protocol B: Aliquots of 50 mg/mL ethanolic solutions of DODAP, DOPE, cholesterol and DMG-PEG2K is mixed and diluted with ethanol to 3 mL final volume. Separately, an aqueous buffered solution (10 mM citrate/150 NaCl, pH 4.5) of EPO mRNA is prepared from a 1 mg/mL stock. The lipid solution is injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.35 mg/mL EPO mRNA (encapsulated). Zave=75.9 nm (Dv(50)=57.3 nm; Dv(90)=92.1 nm).

Protocol C: Aliquots of a 2.0 mg/mL aqueous solution PEI (branched, 25 kDa) is mixed with aqueous solution of CFTR mRNA (1.0 mg/mL). The resulting complexed mixture is pipetted up and down several times and put aside for 20 minutes prior to injection. Final concentration=0.60 mg/mL CFTR mRNA (encapsulated). Zave=75.9 nm (Dv(50)=57.3 inn; Dv(90)=92.1 nm).

II. Analysis of Modified Messenger RNA Versus Unmodified mRNA

II-a. Quantification of Modified Base Within Messenger RNA Construct

4'-Thio NIP modified messenger RNA are subjected to RNase I or Nuclease P1 for various periods of time to allow for sufficient degradation. Upon completion, the resulting monophosphate nucleotides are degraded further with alkaline phosphatase to provide the respective nucleosides. The nucleoside mixture is applied to an Amicon spin column (30,000 MWCO) for efficient enzyme removal. The resulting nucleoside solution is analyzed via HPLC and quantified via peak area comparison with respective unmodified nucleoside.

II-b. Stability of 4'-Thio NTP Modified Messenger RNA Construct

4'-Thio NIP modified messenger RNA is subjected to RNase I or Nuclease P1 for a various periods of time to assess resistance to nuclease degradation. Similarly, 4'-thio NTP modified messenger RNA was treated with serum (containing nucleases) over various time periods to assess nuclease degradation. At specified time points, the nuclease reactions are quenched with inhibitor and the resulting solution is applied to an Amicon spin column (30,000 MWCO) for efficient enzyme removal. Upon completion, the retentate is applied to a 1% agarose gel and analyzed for mRNA construct viability (size, degradation products, etc). Identical experiments are performed on unmodified mRNA and direct comparisons and inferences may be drawn.

II-c. 4'-Thio NIP Modified Messenger RNA Effects on Protein Production

In Vitro Studies: In vitro transfections of 4'-thio NIP modified mRNA and unmodified mRNA are performed using HEK293T cells. Transfections of one microgram of each mRNA construct are performed in separate wells using lipofectamine. Cells are harvested at select time points (ea. 4 hour, 8 hour, 24 hour, 48 hour, 72 hour, etc.) and respective protein production are analyzed. For FFL mRNA, cell lysates are analyzed for luciferase production via bioluminescence assays. For EPO and GLA mRNA studies, cell supernatants are obtained and analyzed for EPO and GLA protein, respectively, using ELISA-based methods. A comparison of protein production over time of unmodified versus 4'-thio NTP modified mRNA may be made.

In Viva Studies: A comparison of protein production over time is made via injection of 4'thio NTP modified mRNA encapsulated nanoparticles (lipid or polymeric) into wild type mice (CD-1) versus unmodified mRNA delivered in identical fashion. Serum and organs were collected at select time points (e.g. 6 hr, 12 hr, 24 hr, 48 hr, 72 hr, etc.) and respective protein levels are monitored. For FFL mRNA, liver homogenates are analyzed for luciferase production via bioluminescence assays. For EPO and GLA mRNA studies, mouse sera are obtained and analyzed for EPO and GLA protein, respectively, using ELISA-based methods. A comparison of protein production over time of unmodified versus 4'-thio NTP modified mRNA is made.

Similarly, unencapsulated (naked) 4'thio NTP modified mRNA and unmodified mRNA are injected via either intravenous, subcutaneous or intratracheal administration and identical analyses may be performed as described above to assess differences of stability and protein production.

III. Analysis of FFL, EPO and GLA Protein Produced Via Administered Naked Modified mRNA or mRNA-Loaded Nanoparticles

III-a. Injection Protocol

All studies are performed using male CD-1 mice of approximately 6-8 weeks of age at the beginning of each experiment. Samples are introduced by a single bolus tail-vein injection of an equivalent total dose of 30-200 micrograms of unencapsulated or encapsulated FFL, EPO or GLA mRNA (modified or unmodified). Mice are sacrificed and perfused with saline at the designated time points.

III-b. Isolation of Organ Tissues for Analysis

The liver and spleen of each mouse is harvested, apportioned into three parts, and stored in either 10% neutral buffered formalin or snap-frozen and stored at −80° C. for analysis.

III-c. Isolation of Serum for Analysis

All animals are euthanized by $CO_2$ asphyxiation 48 hours post dose administration (±5%) followed by thoracotomy and terminal cardiac blood collection. Whole blood (maximal obtainable volume) is collected via cardiac puncture on euthanized animals into serum separator tubes, allowed to clot at room temperature for at least 30 minutes, centrifuged at 22° C.=5° C. at 9300 for 10 minutes, and the serum is extracted. For interim blood collections, approximately 40-504 µf whole blood is collected via facial vein puncture or tail snip. Samples collected from non-treatment animals are used as a baseline GLA levels for comparison to study animals.

III-d. Enzyme-Linked Immunosorbent Assay (ELISA) Analysis

EPO ELISA: Quantification of EPO protein is performed following procedures reported for human EPO ELISA kit (Quantikine IVD, R&D Systems, Catalog # Dep-00). Positive controls that may be employed consist of ultrapure and tissue culture grade recombinant human erythropoietin protein (R&D Systems, Catalog #286-EP and 287-TC, respectively). Blood samples are taken at designated time points and processed as described above. Detection is monitored via absorption (450 nm) on a Molecular Device Flex Station instrument.

GLA ELISA: Standard ELISA procedures are followed employing sheep anti-REPLAGAL® G-188 IgG as the capture antibody with rabbit anti-REPLAGAL® TK-88 IgG as the secondary (detection) antibody (Shire Human Genetic Therapies). Horseradish peroxidase (HRP)-conjugated goat anti-rabbit IgG is used for activation of the 3,3',5,5'-tetramethylbenzidine (TMB) substrate solution. The reaction is quenched using 2N $H_2SO_4$ after 20 minutes. Detection is monitored via absorption (450 nm) on a Molecular Device Flex Station instrument. Untreated mouse serum and human REPLAGAL® protein is used as negative and positive controls, respectively.

III-e. Bioluminescence Analysis

Luciferase Assay: The bioluminescence assay is conducted using a Promega Luciferase Assay System (Item # E1500). The Luciferase Assay Reagent is prepared by adding 10 mL of Luciferase Assay Buffer to Luciferase Assay Substrate and mix via vortex. Approximately 20 uL of homogenate samples are loaded onto a 96-well plate followed by 20 uL of plate control to each sample. Separately, 120 uL of Luciferase Assay Reagent (prepared as described above) is added to each well of a 96-well flat bottomed plate. Each plate is then inserted into the appropriate chambers using a Molecular Device Flex Station instrument and measure the luminescence (measured in relative light units (RLU)).

Example 2

Exemplary Liposome Formulations for Delivery and Expression of mRNA with 4'-Thio Modifications This example provides exemplary liposome formulations for effective delivery and expression of 4'-Thio modified mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate various nucleic acid-based materials. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" *J. Contr. Rel.* 2005, 107, 276-287), DLin-KC2-DMA (Semple, S. C. et al. "Rational Design of Cationic Lipids for siRNA Delivery" *Nature Biotech.* 2010, 28, 172-176), C12-200 (Love, K. T. et al. "Lipid-like materials for low-dose in vivo gene silencing" *PNAS* 2010, 107, 1864-1869), HGT4003, HGT5000, HGT5001, MC3, cKK-E12 (3,6-bis(4-(bis(2-hydroxydodecyl)amino)butyl)piperazine-2,5-dione), ICE, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanotamine), DPPE (1,2-dipalmitoyl-sn-glycero-3-phosphoethanolamine), DMPE (1,2-dimyristol-sn-glycero-3-phosphoethanolamine), DOPG (,2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

Polymeric Materials

Further formulations described herein include various charged, polymeric materials which can include (but not exclusively) branched polyethyleneimine (PEI) (25 kDa) (Sigma #408727), protamine, PEGylated protamine, PLL, PEGylated PLL, etc.

mRNA Materials

Firefly Luciferase (FFL), human erythropoietin (EPO) and human alpha-galactosidase (GLA) were synthesized by in vitro transcription from a plasmid DNA template encoding the gene, which was followed by the addition of a 5' cap structure (Cap1) (Fechter, P.; Brownlee, G. G. "Recognition of mRNA cap structures by viral and cellular proteins" *J. Gen. Virology* 2005, 86, 1239-1249) and a 3' poly(A) tail of approximately 200 nucleotides in length as determined by gel electrophoresis. 5' and 3' untranslated regions present in each mRNA product are represented as X and Y, respectively and defined as stated (vide infra).

Exemplary mRNA sequences of human erythropoietin (EPO), human alpha-galactosidase (GLA) and Codon-Optimized Firefly Luciferase (FFL) are depicted in SEQ ID No. 1, 2, and 3, respectively. Exemplary 5' and 3' UTR sequences are described in SEQ ID Nos. 4, 5, 6, and 7.

Exemplary Formulation Protocols

A. C12-200 and GLA

Aliquots of 50 mg/mL ethanolic solutions of C12-200, DOPE, cholesterol and DMG-PEG2K were mixed and diluted with ethanol to 3 mL final volume. Separately, an aqueous buffered solution (0 mM citrate/150 mM NaCl, pH 4.5) of GLA mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated, and stored at 2-8° C. Final concentration=0.85 mg/mL GLA mRNA (encapsulated). $Z_{ave}$=81.2 nm ($Dv_{(50)}$=63.2 nm; $Dv_{(90)}$=104 nm).

B. DODAP and EPO

Aliquots of 50 mg/mL ethanolic solutions of DODAP, DOPE, cholesterol and DMG-PEG2K were mixed and diluted with ethanol to 3 mL final volume. Separately, an aqueous buffered solution (10 mM citrate/150 mM NaCl, pH 4.5) of EPO mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated, and stored at 2-8° C. Final concentration=1.35 mg/mL EPO mRNA (encapsulated). $Z_{ave}$=75.9 nm ($Dv_{(50)}$=57.3 nm; $Dv_{(90)}$=92.1 nm).

C. PEI and CFTR

Aliquots of a 2.0 mg/mL aqueous solution PEI (branched, 25 kDa) were mixed with aqueous solution of CFTR mRNA (1.0 mg/mL). The resulting complexed mixture was pipetted up and down several times and put aside for 20 minutes prior to injection. Final concentration=0.60 mg/mL CFTR mRNA (encapsulated). $Z_{ave}$=75.9 nm ($Dv_{(50)}$=57.3 nm; $Dv_{(90)}$=92.1 nm).

Example 3

Analysis of In Vivo Stability and Protein Production of Modified mRNA Versus Unmodified mRNA This example illustrates exemplary methods for analyzing stability of modified mRNA and protein expression in various target tissues in vivo.

Quantification of Modified Base within mRNA Construct

4'-Thio NIP Modified mRNA were subjected to RNase I or Nuclease P1 for various periods of time to allow for sufficient degradation. Upon completion, the resulting monophosphate nucleotides were degraded further with alkaline phosphatase to provide the respective nucleosides. The nucleoside mixture was applied to an Amicon spin column (30,000 MWCO) for efficient enzyme removal. The resulting nucleoside solution was analyzed via HPLC and quantified via peak area comparison with respective unmodified nucleoside.

Stability of 4'-Thio NTP mRNA Construct

4'-Thio NIP Modified mRNA were subjected to RNase I or Nuclease P1 for a various periods of time to assess resistance to nuclease degradation. At specified time points, the nuclease reactions were quenched with inhibitor and the resulting solution was applied to an Amicon spin column (30,000 MWCO) for efficient enzyme removal. Upon completion, the retentate was applied to a 1% agarose get and analyzed for mRNA construct viability (size, degradation products, etc). Identical experiments were performed on unmodified mRNA and direct comparisons and inferences were drawn.

4'-Thio NTP Modified mRNA Effects on Protein Production

In Vitro Studies

Figure 2:
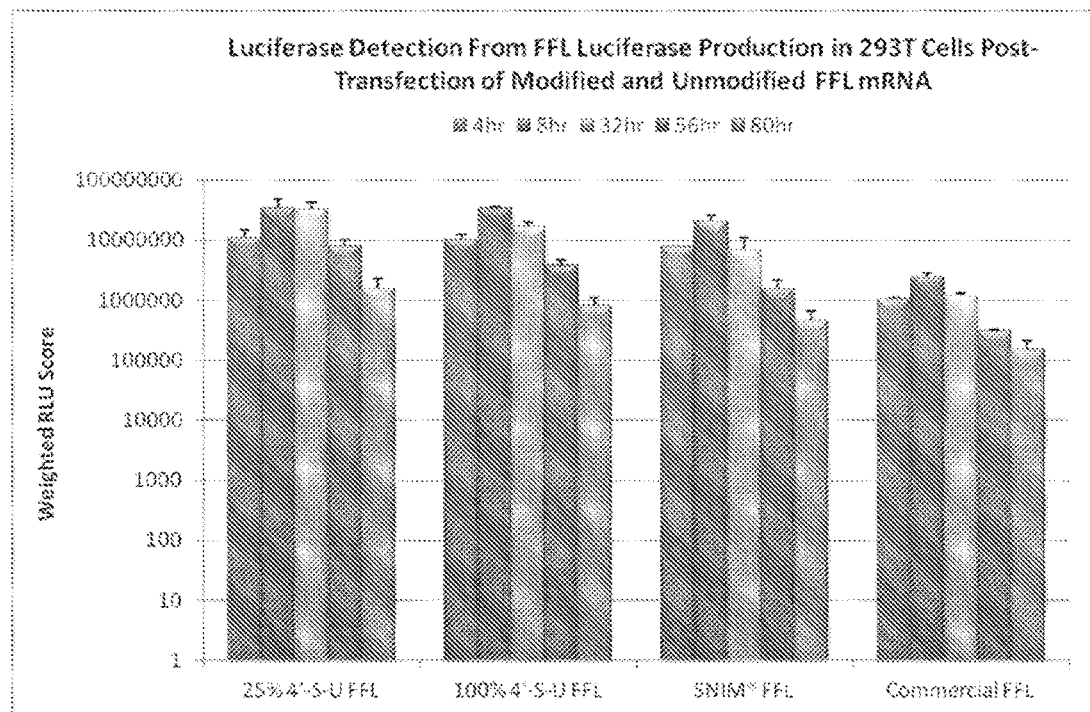
FIG. 2 shows luciferase detection from FFL luciferase production in HEK 293T cells post-transfection of modified and unmodified FFL mRNA.

In vitro transfections of 4'-thio NTP modified mRNA and unmodified mRNA were performed using HEK293T cells. Transfections of one microgram of each mRNA construct were performed in separate wells using lipofectamine. Cells were harvested at select time points (e.g. 4 hour, 8 hour, 32 hour, 48 hour, 56 hour, 80 hour, etc.) and respective protein production was analyzed. For FFL mRNA, cell lysates were analyzed for luciferase production via bioluminescence assays. For EPO and GLA mRNA studies, cell supernatants were obtained and analyzed for EPO and GLA protein, respectively, using ELISA-based methods. A comparison of protein production over time of unmodified versus 4'-thio NTP modified mRNA was made. Exemplary results are shown in FIG. 2.

In Vivo Studies

A comparison of protein production over time was made via injection of 4'thio NTP modified mRNA encapsulated nanoparticles (lipid or polymeric) into wild type mice (CD-1) versus unmodified mRNA delivered in an identical fashion. Serum and organs were collected at select time points (e.g. 6 hr, 12 hr, 24 hr, 48 hr, 72 hr, etc.) and respective protein levels were monitored. For FFL mRNA, liver homogenates were analyzed for luciferase production via bioluminescence assays. For EPO and GLA mRNA studies, mouse sera were obtained and analyzed for EPO and GLA protein, respectively, using ELISA-based methods. A comparison of protein production over time of unmodified versus 4'-thio NTP modified mRNA was made.

Similarly, unencapsulated (naked) 4'thio NTP modified mRNA and unmodified mRNA were injected via either intravenous, subcutaneous or intratracheal administration and identical analyses were performed to assess differences in stability and protein production.

Example 4

Analysis of FFL, EPO and GLA Protein Production after Administration of Naked Modified mRNA or mRNA-Loaded Nanoparticles This example describes the protocol for analyzing exemplary protein production after administering either naked, modified, mRNA or mRNA-loaded nanoparticles and demonstrates mRNA stability and protein production for 4'-thio modified mRNA compared to unmodified mRNA.

All studies were performed using male CD-1 mice of approximately 6-8 weeks of age at the beginning of each experiment. Samples were introduced by a single bolus tail-vein injection of an equivalent total dose of 30-200 micrograms of unencapsulated or encapsulated FFL, EPO or GLA mRNA (modified or unmodified). Mice were sacrificed and perfused with saline at the designated time points.

The liver and spleen of each mouse was harvested, apportioned into three parts, and stored in either 10% neutral buffered formalin or snap-frozen and stored at −80° C. for analysis.

All animals were euthanized by $CO_2$ asphyxiation 48 hours post dose administration (±5%) followed by thoracotomy and terminal cardiac blood collection. Whole blood (maximal obtainable volume) was collected via cardiac puncture from euthanized animals into serum separator tubes, allowed to clot at room temperature for at least 30 minutes, centrifuged at 22° C.±5° C. at 9300 g for 10 minutes, after which time serum was extracted. For interim blood collections, approximately 40-50 µL of whole blood was collected via facial vein puncture or tail snip. Samples collected from non-treatment animals were used for baseline GLA levels for comparison to study animals.

Enzyme-Linked Immunosorbent Assay (ELISA) Analysis

Quantification of EPO protein was performed following procedures reported for human EPO ELISA kit (Quantikine IVD, R&D Systems, Catalog # Dep-00). Positive controls employed consisted of ultrapure and tissue culture grade recombinant human erythropoietin protein (R&D Systems, Catalog #286-EP and 287-TC, respectively). Blood samples were taken at designated time points and processed as described above. Detection was monitored via absorption (450 nm) on a Molecular Device Flex Station instrument.

For analysis of GLA protein, standard ELISA procedures were followed employing sheep anti-Replagal G-188 IgG as the capture antibody with rabbit anti-Replagal IgG as the secondary (detection) antibody. Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 20 minutes. Detection was monitored via absorption (450 nm) on a Molecular Device Flex Station instrument. Untreated mouse serum and human Replagal® protein were used as negative and positive controls, respectively.

Bioluminescence Analysis

The bioluminescence assay was conducted using a Promega Luciferase Assay System (Item # E1500). The Luciferase Assay Reagent was prepared by adding 10 mL of Luciferase Assay Buffer to Luciferase Assay Substrate and mixed via vortex. 20 uL of homogenate samples were loaded onto a 96-well plate followed by 20 uL of plate control to each sample. Separately, 120 uL of Luciferase Assay Reagent (prepared as described above) was loaded into each well of a 96-well flat bottomed plate. Each plate was then inserted into the appropriate chambers using a Molecular Device Flex Station instrument and the luminescence was measured in relative light units (RLU).

Exemplary Results

The production of FFL protein via transfection of 4'-thio modified or unmodified FFL mRNA was tested in HEK 293T cells. FIG. 2 represents the weighted relative fluorescence units (RLU) scores taken 4 hours. 8 hours, 32 hours, 56 hours and 80 hours after transfection. At each time point, cells transfected with either 25% 4'-thio uridine (25% 4'-S-U) or 100% 4'-thio uridine (100% 4'-S-U) FFL mRNA had higher weighted RLU scores than cells transfected with either SNIM® FFL or commercial FFL.

Figure 3:
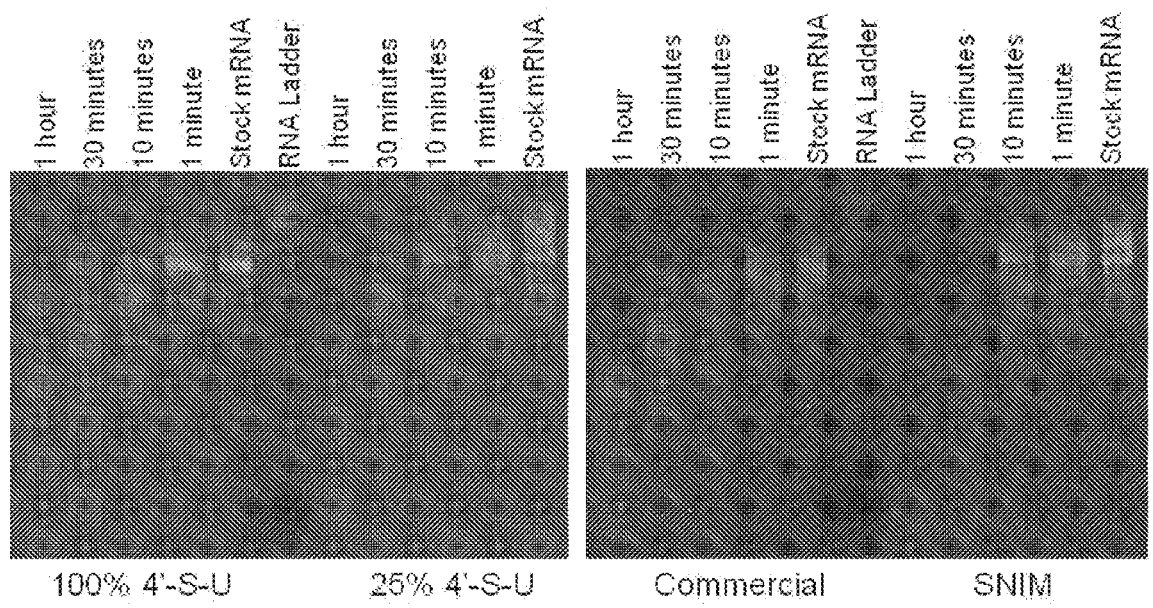
FIG. 3 shows the results of a stability study of modified and unmodified FFL mRNA.

The stability of 4'-thio modified and unmodified FFL mRNA over time was also tested. Three micrograms of mRNA were exposed to mouse serum and monitored over the course of one hour. As can be seen in FIG. 3, compared to SNIM® FFL and commercial FFL mRNA, 4'-thio modified mRNA, particularly 100% 4'-thio uridine (100% 4'-S-U) FFL mRNA, appears to be more stable over time.

Figure 4:
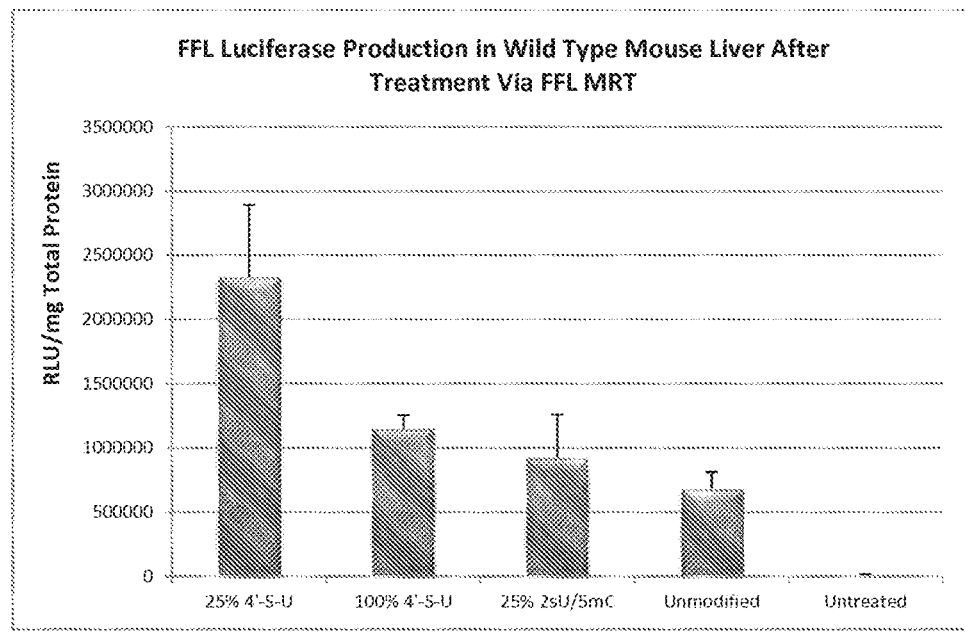
FIG. 4 shows luciferase detection from FFL luciferase production in mouse liver post-administration of modified and unmodified FFL mRNA.

The production of FFL protein via transfection of 4'-thio modified or unmodified FFL mRNA was tested in wild-type mice. A 1.0 mg/kg dose of C12-200-loaded lipid nanoparticles was administered intravenously and animals were sacrificed and their livers were removed for analysis, as described above. FIG. 4 represents RLU/mg Total Protein scores taken six hours post-administration. Livers from mice treated with 25% 4'-thio uridine (25% 4'-S-U) and 100% 4'-thio uridine (100% 4'-S-U) had higher RLU/mg scores than the livers from mice treated with unmodified mRNA.

Among other things, the exemplary results described herein demonstrated that a provided mRNA comprising 4'-thio-modified nucleotide can be successfully synthesized, have increased stability, and can be used successfully to produce protein in cells.

Example 5

Exemplary Syntheses of 4'-Thio-Modified Nucleotides

Synthetic Procedures

Preparation of Intermediates

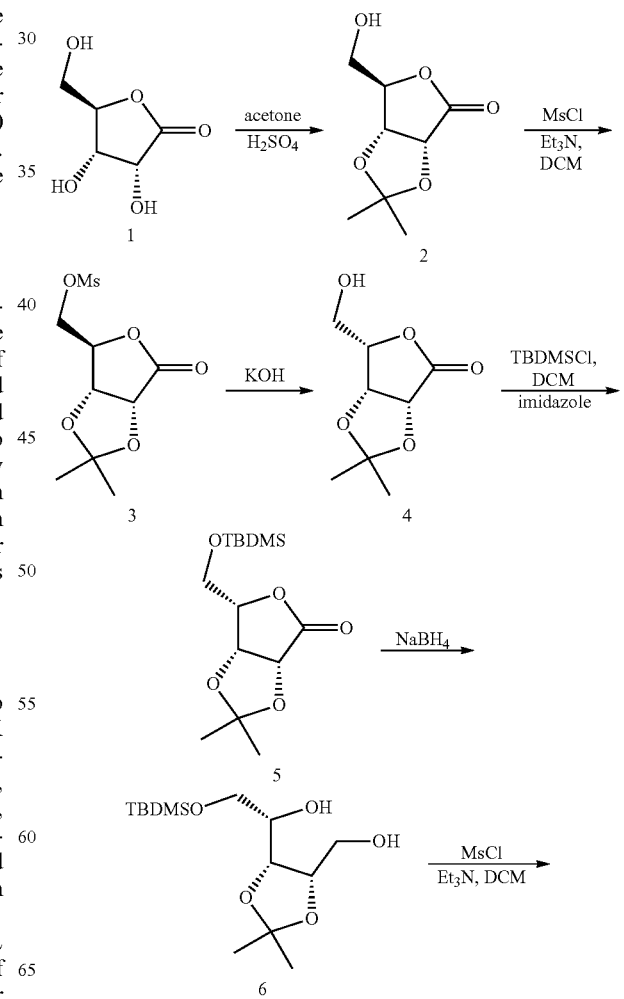

-continued

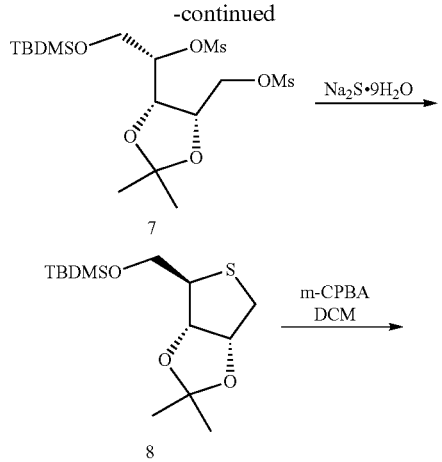

Synthesis of 2,3-O-isopropylidene-D-ribonic acid-1,4-lactone

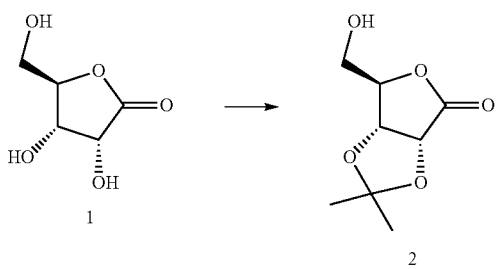

Carbohydrate Research 2008, 1790-1800

A solution of D-ribonic acid-1,4-lactone (270.0 g, 1,823 mol) and sulphuric acid (18.0 g, 0.182 mol, 0.1 equiv.) in acetone (2.79 L) was stirred at room temperature for 3 days. The reaction mixture was quenched by the addition of solid sodium bicarbonate (~450 g), filtered and the filtrate evaporated. The residue was partitioned between ethyl acetate and water. The aqueous layer was extracted with ethyl acetate; the combined organic layers were dried over magnesium sulphate, filtered and concentrated under reduced pressure to give the desired product as a white solid (318.8 g, 93%). $^1$H NMR (300 MHz, CDCl$_3$) δ 4.83 (d, J=5.5 Hz, 1H), 4.77 (d, J=5.5 Hz, 1H), 4.64-4.62 (m, 1H), 3.99 (ddd, J=2.3, 5.5 and 12.4 Hz, 1H), 3.81 (ddd, J=2.3, 5.5 and 12.4 Hz, 1H), 2.67 (t, J=5.5 Hz, 1H), 1.46 (s, 3H), 1.37 (s, 3H).

Synthesis of 5-O-methanesulfonyl-2,3-O-isopropylidene-D-ribonic acid-1,4-lactone

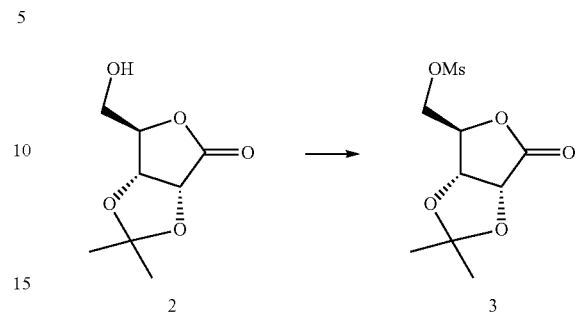

Organic Process Research and Development 2006, 487-492

Methanesulfonyl chloride (116.0 g, 1.014 mol, 1.2 equiv.) was added dropwise at 0° C. to a solution of 2,3-O-isopropylidene-D-ribonic acid-1,4-lactone (159.0 g, 0.845 mol) and triethylamine (128.0 g, 1.267 mol) an dichloromethane (2.43 L). The reaction mixture was stirred at room temperature for 1 h. and was then diluted with dichloromethane and washed with water, sat. aq. NaHCO$_3$ and brine. The organic layer was dried over magnesium sulphate, filtered and concentrated under reduced pressure to give 5-O-methanesulfonyl-2,3-O-isopropylidene-D-ribonic acid-1,4-lactone as an orange oil (231.0 g, ca. 100%). $^1$H NMR (300 MHz, CDCl$_3$) δ 4.82-4.77 (m, 3H), 4.49-4.41 (m, 2H), 3.04 (s, 3H), 1.47 (s, 3H), 1.38 (s, 3H).

Synthesis of 2,3-O-isopropylidene-L-lyxonic acid-1,4-lactone

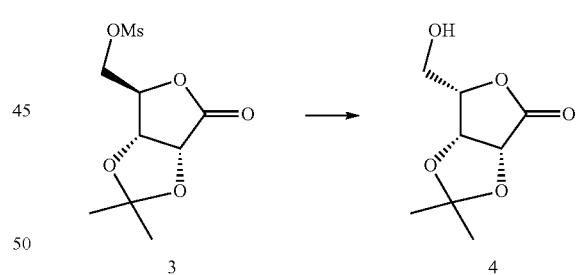

Organic Process Research and Development 2006, 487-492

Potassium hydroxide 137.0 g, 2.45 mol) in water (1.1 L) was added to 5-O-methanesulfonyl-2,3-O-isopropylidene-D-ribonic acid-1,4-lactone (225.0 g, 0.85 mol) and stirred at room temperature for 18 h. The reaction mixture was acidified to pH 3 with 2 M aq. HCl (using a pH meter) then evaporated. The residue was heated to reflux in acetone and the acetone decanted (×3). The combined extracts were dried over magnesium sulphate, filtered and concentrated under reduced pressure to give 2,3-O-isopropylidene-L-lyxonic acid-1,4-lactone as a pale yellow solid (115.4 g, 73%). $^1$H NMR (300 MHz, CDCl$_3$) δ 4.89-4.84 (m, 2H), 4.63-4.59 (m, 1H), 4.08-3.91 (m, 2H), 1.46 (s, 3H), 1.38 (s, 3H).

Synthesis of 5-O-tert-butyldimethylsilyl-2,3-O-isopropylidene-L-lyxonic acid-1,4-lactone

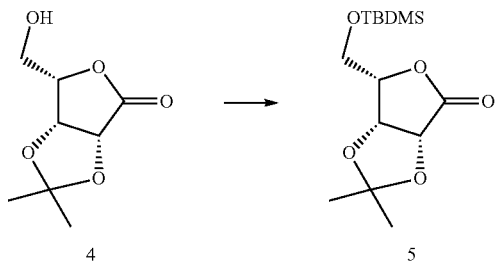 [SMILES: CC1(C)O[C@@H]2[C@H](CO)OC(=O)[C@@H]2O1 ; CC1(C)O[C@@H]2[C@H](CO[Si](C)(C)C(C)(C)C)OC(=O)[C@@H]2O1]

Carbohydrate Research 2008, 1790-1800

To a solution of 2,3-O-isopropylidene-L-lyxonic acid-1,4-lactone (5.0 g, 0.027 mol) in dichloromethane (85.0 ml) was added imidazole (2.2 g, 32 mmol) followed by tert-butyldimethyllsilyl chloride (4.4 g, 29 mmol, 1.1 equiv.) and the reaction mixture stirred at room temperature for 1.5 h. The reaction mixture was diluted with dichloromethane, washed with sat. aq. NaHCO$_3$, brine, dried over magnesium sulphate, filtered and concentrated under reduced pressure to give 5-O-tert-butyldimethylsilyl-2,3-O-isopropylidene-L-lyxonic acid-1,4-lactone as a pale yellow oil (7.3 g, 89%). $^1$H NMR (300 MHz, CDCl$_3$) δ 4.79 (s, 2H), 4.54-4.49 (m, 1H), 4.00-3.86 (m, 2H), 1.45 (s, 3H), 1.38 (s, 3H), 0.89 (s, 9H), 0.08 (s, 6H).

Synthesis of 5-O-tert-butyldimethylsilyl-2,3-O-isopropylidene-L-lyxitol

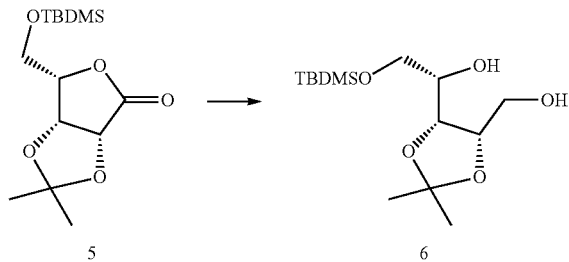 [SMILES: CC1(C)O[C@@H]2[C@H](CO[Si](C)(C)C(C)(C)C)OC(=O)[C@@H]2O1 ; CC1(C)O[C@H]([C@@H](O)CO[Si](C)(C)C(C)(C)C)[C@H](CO)O1]

Carbohydrate Research 2008, 1790-1800

To a solution of 5-O-tert-butyldimethylsilyl-2,3-O-isopropylidene-L-lyxonic acid-1,4-lactone (7.2 g, 24 mmol) in tetrahydrofuran (63 ml) and methanol (13 ml) was added sodium borohydride (1.4 g, 0.036 mol, 1.5 equiv.) portion-wise at room temperature. The reaction mixture was stirred for 1 h at room temperature and then concentrated under reduced pressure. The residue was partitioned between ethyl acetate and 1 M aq. citric acid. The organic layer was washed with 1 M aq. citric acid, brine, dried over magnesium sulphate, tittered and concentrated under reduced pressure to give 5-O-tert-butyldimethylsilyl-2,3-O-isopropylidene-L-lyxitol as a colourless oil which crystallised upon standing (6.3 g, 86%). $^1$H NMR (300 MHz, CDCl$_3$) 4.26-4.20 (m, 2H), 3.84-3.59 (m, 5H), 1.51 (s, 3H), 1.37 (s, 3H), 0.89 (s, 9H), 0.07 (s, 6H).

Synthesis of 5-O-tert-butyldimethylsilyl-2,3-O-isopropylidene-1,4-di-O-methanesulfonyl-L-lyxitol

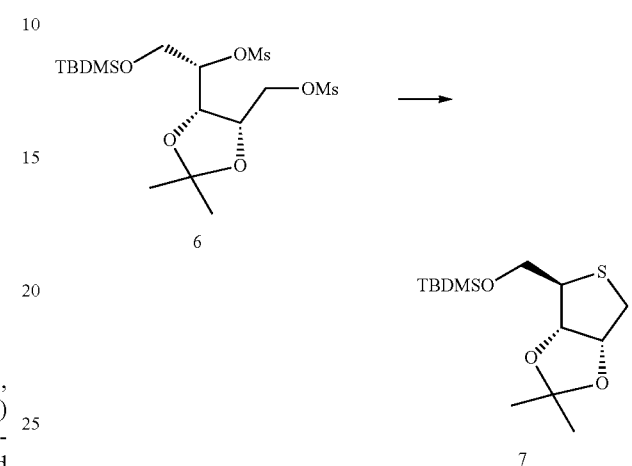

Carbohydrate Research 2008, 1790-1800

Methanesulfonyl chloride (15.2 ml, 0.196 mol, 10 equiv.) was added drop-wise at <10° C. to pyridine (15.8 ml, 0.196 mol, 10 equiv.). A solution of 5-O-tert-butyldimethylsilyl-2,3-O-isopropylidene-L-lyxitol (6 g, 0.0196 mol) in dichloromethane (16 ml) was added drop-wise at <10° C. The reaction mixture was stirred at rt for 2 h. The cooling bath was replaced and the excess of methanesulfonyl chloride was hydrolyzed by addition of ice. The reaction mixture was then poured in water (300 mL) and extracted with Et$_2$O (3×50 mL). The combined organic layers were washed with 1 M aq. citric acid, sat. aq. NaHCO$_3$ and brine, dried (MgSO$_4$), filtered and concentrated under reduced pressure. The crude product was purified by flash chromatography on silica gel with 1:6 ethyl acetate/heptane to give 5-O-tert-butyldimethylsilyl-2,3-O-isopropylidene-1,4-di-O-methanesulfonyl-L-lyxitol as yellow oil (8 g, 91%). $^1$H NMR (300 MHz, CDCl$_3$) δ 4.76-4.69 (m, 1H), 4.46-4.34 (m, 4H), 3.95 (dd, J=5.5 and 11.0 Hz, 1H), 3.82 (dd, J=6.0 and 11.0 Hz, 1H), 3.11 (s, 3H), 3.07 (s, 3H), 1.51 (s, 3H), 1.37 (s, 3H), 0.89 (s, 9H), 0.09 (s, 6H).

Synthesis of tert-butyl((3aS,4R,6aR)-2,2-dimethyltetrahydrothieno[3,4-d][1,3]dioxol-4-yl)methoxy)dimethylsilane

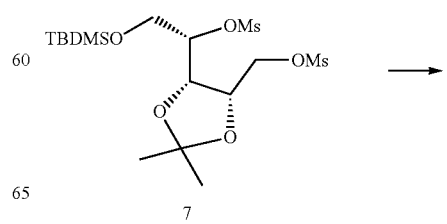

-continued

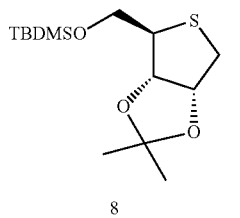

8

To a solution of 5-O-tert-butyldimethylsilyl-2,3-O-isopropylidene-1,4-di-O-methanesulfonyl-L-lyxitol (25.1 g, 0.056 mol) in dimethylformamide (250 ml) was added Na$_2$S.9H$_2$O (16.1 g, 0.067 mol, 1.2 eq.) and the reaction mixture was heated at 80° C. for 3 h. The reaction mixture was cooled to room temperature, partitioned between water and ethyl acetate. The layers were separated and the aqueous layer was extracted with ethyl acetate. The combined organic layers were dried (MgSO$_4$), filtered and concentrated under reduced pressure. The crude product was purified by flash chromatography on silica gel with ethyl acetate/heptane (10:1) to give tert-butyl(((3aS,4R,6aR)-2,2-dimethyltetrahydrothieno[3,4-d][1,3]dioxol-4-yl)methoxy)-dimethylsilane (10.3 g, 60%), $^1$H NMR (300 MHz, CDCl$_3$) δ 4.89 (dt, J=1.4 and 4.6 Hz, 1H), 4.79 (d, J=6.0 Hz, 1H), 3.80 (dd, J=5.0 and 10.5 Hz, 1H), 3.60 (dd, J=6.4 and 1.0.6 Hz, 1H), 3.33 (t, J=5.0 Hz, 1H), 3.16 (dd, J=5.0 and 12.4 Hz, 1H), 2.85 (dd, J=0.9 and 12.8 Hz, 1H), 1.52 (s, 3H), 1.32 (s, 3H), 0.89 (s, 9H), 0.06 (s, 6H).

Synthesis of (3aS,4R,5R,6aR)-4-(((tert-butyldimethylsilyl)oxy)methyl)-2,2-dimethyltetrahydrothieno[3,4-d][1,3]dioxole 5-oxide

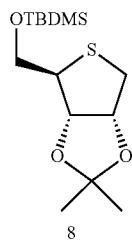 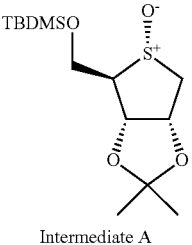

8      Intermediate A

A solution of ca 70% m-chloroperbenzoic acid (16 g, 66 mmol) in dichloromethane (150 ml) was dried over magnesium sulphate and filtered. After washing with dichloromethane (50 ml), the combined filtrate was added dropwise to a solution of tert-butyl(((3aS,4R,6aR)-2,2-dimethyltetrahydrothieno[3,4-d][1,3]dioxol-4-yl)methoxy)dimethylsilane (20 g, 66 mmol) in dichloromethane (400 ml) at 78° C. After stirring for an hour at −78° C., the reaction was quenched with saturated sodium bicarbonate solution and diluted with dichloromethane. The layers were separated and the organic washed with brine, dried over magnesium sulphate, filtered and concentrated. The residue obtained was purified by flash chromatography (silica gel/dichloromethane: diethyl ether (30:1) to give (3aS,4R,5S,6aR)-4-(((tert-butyldimethylsilyl)oxy)methyl)-2,2-dimethyltetrahydrothieno[3,4-d][1,3]dioxole 5-oxide (8.8 g, 42%) and (3aS,4R,5R,6aR)-4-(((tert-butyldimethylsilyl)oxy)methyl)-2,2-dimethyltetra-hydrothieno[3,4-d][1,3]dioxole 5-oxide (7.3 g, 35%).

Synthesis of Nucleoside Intermediates 1-((3aR,4R,6R,6aS)-6-(hydroxymethyl)-2,2-dimethyltetrahydrothieno[3,4-d][1,3]dioxol-4-yl)pyrimidine-2,4(1H,3H)-dione

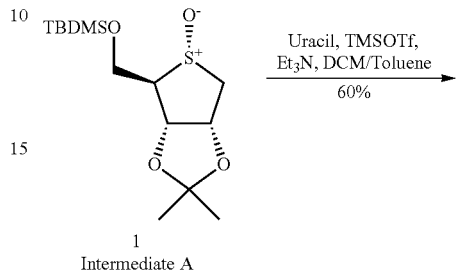

1
Intermediate A

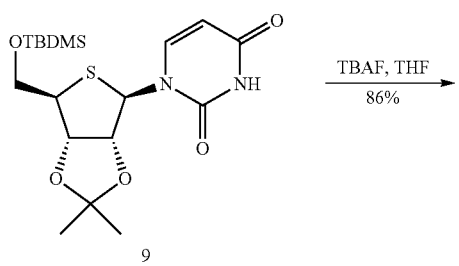

9

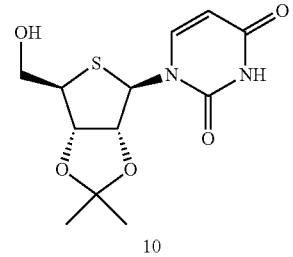

10

Synthesis of 1-((3aR,4R,6R,6aS)-6-(((tert-butyldimethylsilyl)oxy)methyl)-2,2-dimethyl-tetrahydrothieno[3,4-d][1,3]dioxol-4-yl)pyrimidine-2,4(1H,3H)-dione

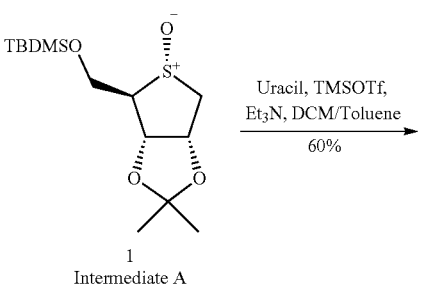

1
Intermediate A

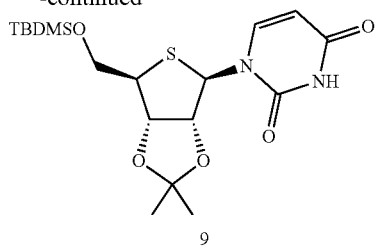

9

To a suspension of uracil (1.40 g, 12.5 mmol) in toluene (62 was added triethylamine (3.5 ml, 2.53 g, 25 mmol) and trimethylsilyl trifluoromethanesulfonate (9.01 ml, 11.1 g, 50 mmol). After stirring for an hour at room temperature, dichloromethane (34 ml) was added to the bi-phasic mixture to give a solution; this was then added drop-wise to a solution of (3aS,4R,5R,6aR)-4-(((tert-butyldimethylsilyl)oxy)methyl)-2,2-dimethyltetrahydrothieno[3,4-d][1,3]dioxole 5-oxide (2.0 g, 6.25 mmol) in dichloromethane (34 ml) and then triethylamine (3.5 ml, 25 mmol) was added. After stirring for 90 minutes at room temperature, the reaction was quenched with ice and then diluted with ethyl acetate. The layers were separated and the organic washed with saturated sodium bicarbonate solution (×2) and then brine. After drying over magnesium sulphate, concentration under reduced pressure gave crude product which was purified by flash chromatography (silica gel, ethyl acetate:dichloromethane 1:5) to give 1-((3aR,4R,6R,6aS)-6-(((tert-butyldimethylsilyl)oxy)methyl)-2,2-dimethyl-tetrahydrothieno[3,4-d][1,3]dioxol-4-yl)pyrimidine-2,4(1H,3H)-dione (1.55 g, 60%), $^1$H NMR (300 MHz, CDCl$_3$) δ 8.43 (s, 1H), 7.96 (d, J=8.3 Hz, 1H), 6.12 (d, J=2.3 Hz, 1H), 5.74 (dd, J=1.9 and 7.8 Hz, 1H), 4.71 (m, 2H), 3.89 (m, 2H), 3.74 (m, 1H), 1.60 (s, 3H), 1.32 (s, 3H), 0.92 (s, 9H), 0.11 (s, 3H), 0.10 (s, 3H).

Synthesis of 1-((3aR,4R,6R,6aS)-6-(hydroxymethyl)-2,2-dimethyltetrahydrothieno[3,4-d][1,3]dioxol-4-yl)pyrimidine-2,4(1H,3H)-dione A solution of 1-((3aR,4R,6R,6aS)-6-(((tert-butyldimethylsilyl)oxy)methyl)-2,2-dimethyl-tetrahydrothieno[3,4-d][1,3]dioxol-4-yl)pyrimidine-2,4(1H,3H)-dione (3.70 g, 8.92 mmol) in tetrahydrofuran (85 ml) was cooled in an ice bath under argon; a solution of 1 M tetrabutylammonium fluoride in tetrahydrofuran (10.7 ml, 10.7 mmol) was added and the mixture stirred for 2 hrs at room temperature. The crude product was collected by filtration, washed with tetrahydrofuran and purified by flash chromatography (silica gel; methanol:dichloromethane 1:30) to give 1-((3aR,4R,6R,6aS)-6-(hydroxymethyl)-2,2-dimethyltetrahydrothieno[3,4-d][1,3]dioxol-4-yl)pyrimidine-2,4(1H,3H)-dione (2.30 g, 86%). $^1$H NMR (300 MHz, CDCl$_3$)(δ 8.97 (brs, 1H), 7.76 (d, J=8.3 Hz, 1H), 5.93 (s, 1H), 5.76 (d, J=8.3 Hz), 4.91 (s, 2H), 3.96 (dd, J=4.6 and 11.0 Hz, 1H), 3.89 (dd, J=4.6 and 11.0 Hz, 1H), 3.79 (t, J=4.6 Hz, 1H), 2.64 (brs, 1H), 1.59 (s, 3H), 1.33 (s, 3H).

4-Amino-1-((3aR,4R,6R,6aS)-6-(hydroxymethyl)-2,2-dimethyltetrahydrothieno[3,4-d][1,3]dioxol-4-yl)-5-methylpyrimidin-2(1H)-one

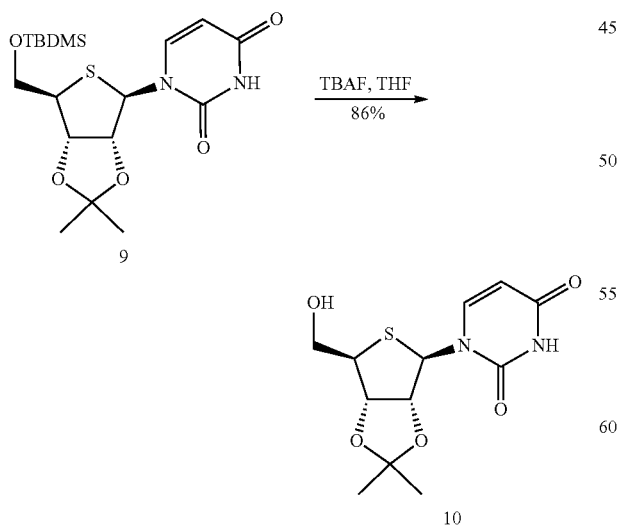

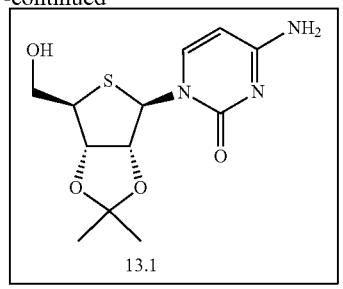

Using a procedure analogous to the following, but substituting cytosine for thymine, 4-amino-1-((3aR,4R,6R,6aS)-6-(hydroxymethyl)-2,2-dimethyltetrahydrothieno[3,4-d][1,3]dioxol-4-yl) pyrimidin-2(1H)-one (13.1) can be synthesized.

Synthesis of 1-((3aR,4R,6R,6aS)-6-(((tert-butyldimethylsilyl)oxy)methyl)-2,2-dimethyltetrahydrothieno[3,4-d][1,3]dioxol-4-yl)-5-methylpyrimidine-2,4(1H,3H)-dione

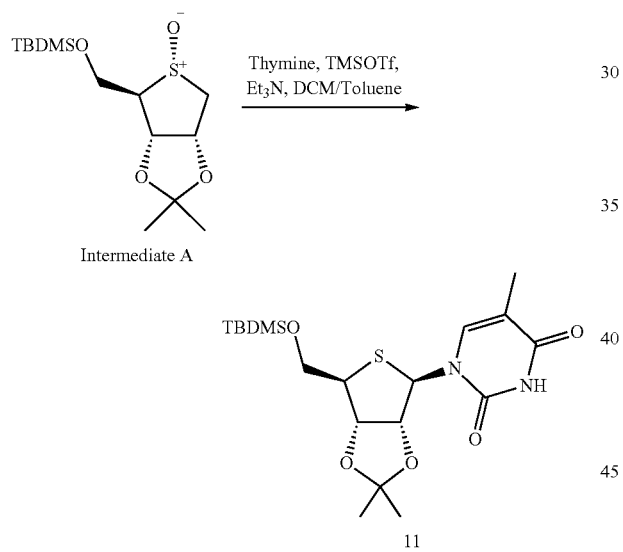

To a suspension of thymine (2.60 g, 20.6 mmol) in toluene (112 ml) was added triethylamine (4.17 g, 41.2 mmol) and trimethylsilyl trifluoromethanesulfonate (18.3 g 82.5 mmol). After stirring for an hour at room temperature, dichloromethane (34 ml) was added to the bi-phasic mixture to give a solution; this was then added drop-wise to a solution of (3aS,4R,5R,6aR)-4-(((tert-butyldimethylsilyl)oxy)methyl)-2,2-dimethyltetrahydrothieno[3,4-d][1,3]dioxole 5-oxide (3.30 g, 10.3 mmol) in dichloromethane (56 ml) and then triethylamine (4.17 g, 41.2 mmol) was added. After stirring for 60 min at room temperature, the reaction was quenched with ice and then diluted with ethyl acetate. The layers were separated and the organic washed with saturated sodium bicarbonate solution (×2) and then brine. After drying over magnesium sulphate, concentration under reduced pressure gave crude product which was purified by flash chromatography (silica gel, ethyl acetate:heptane 0-50%) to give 1-((3aR,4R,6R,6aS)-6-(((tert-butyldimethylsilyl)oxy)methyl)-2,2-dimethyltetrahydrothieno[3,4-d][1,3]dioxol-4-yl)-5-methylpyrimidine-2,4(1H,3H)-dione (2.9 g, 66%). $^1$H NMR (300 MHz, CDCl$_3$) δ 8.43 (s, 1H), 7.46 (d, J=1.4 Hz, 1H), 6.07 (d, J=32 Hz, 1H), 5.72 (m, 2H), 3.87 (m, 2H), 3.71 (m, 11H), 1.93 (s, 3H), 1.59 (s, 3H), 1.32 (s, 3H), 0.92 (s, 9H), 0.10 (s, 3H), 0.09 (s, 3H).

Synthesis of 4-amino-4-((3aR,4R,6R,6aS)-6-(((tert-butyldimethylsilyl)oxy)methyl)-2,2-dimethyltetrahydrothieno[3,4-d][1,3]dioxol-4-yl)-5-methylpyrimidin-2(1H)-one

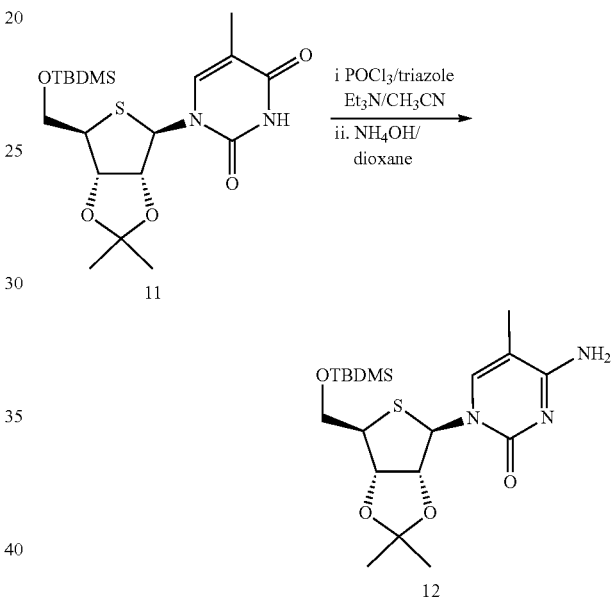

A suspension of 1,2,4-triazole (6.55 g, 94.8 mmol) in acetonitrile (140 ml) was cooled in art ice batch to 0° C.; phosphorus oxychloride (2.53 ml, 27.1 mmol) was added dropwise followed by triethylamine (18.9 ml, 135 mmol). The mixture was stirred at 0° C. for 30 min and then a solution of 1-((3aR,4R,6R,6aS)-6-(((tert-butyldimethylsilyl)oxy)methyl)-2,2-dimethyltetrahydrothieno[3,4-d][1,3]dioxol-4-yl)-5-methylpyrimidine-2,4(1H,3H)-dione (2.9 g, 6.77 mmol) in acetonitrile (25 ml) was added dropwise. The reaction was allowed to warm to room temperature and stirred for 150 min and was then partitioned between ethyl acetate and saturated sodium bicarbonate solution. The organic layer was washed with brine, dried over magnesium sulphate, filtered and concentrated. The residue obtained was dissolved in dioxane (62 ml) in an autoclave; ammonium hydroxide (62 ml) was added and the vessel sealed and stirred overnight at room temperature. The reaction mixture was partitioned between ethyl acetate and water; the organic layer was washed with brine, dried over magnesium sulphate and concentrated under reduced pressure. Purification by flash chromatography (silica gel:methanol:ethyl acetate 1:10) give amino-1-((3aR,4R,6R,6aS)-6-(((tert-butyldimethylsilyl)oxy)methyl)-2,2-dimethyltetrahydrothieno[3,4-d][1,3]dioxol-4-yl)-5-methylpyrimidin-2(1H)-one (2.60 g, 90%). $^1$H NMR (300 MHz, CDCl$_3$) δ 8.74 (brs, 2H), 7.49 (s, 1H), 6.00 (d, J=2.3 Hz, 1H), 4.82 (dd, J=2.3 and 5.5 Hz, 1H), 4.74 (dd, J=3.2 and 5.5 Hz, 1H), 3.91 (dd, J=5.5 and 10.5 Hz, 1H), 3.81 (dd, J=6.4 and 10.5 Hz, 1H), 3.65 (m, 1H), 1.91 (s, 3H), 1.56 (s, 3H), 1.27 (s, 3H), 0.89 (s, 9H), 0.07 (s, 3H), 0.06 (s, 3H).

Synthesis of 4-amino-1-((3aR,4R,6R,6aS)-6-(hydroxymethyl)-2,2-dimethyltetrahydrothieno[3,4-d][1,3]dioxol-4-yl)-5-methylpyrimidin-2(1H)-one

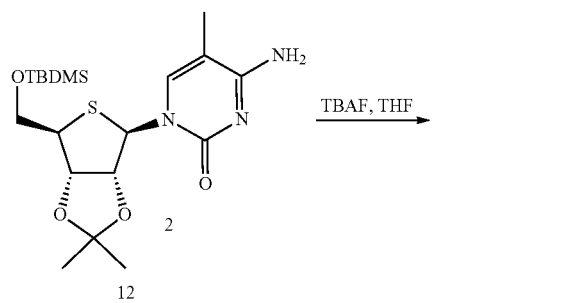

A solution of 4-amino-1-((3aR,4R,6R,6aS)-6-(((tert-butyldimethylsilyl)oxy)methyl)-2,2-dimethyltetrahydrothieno[3,4-d][1,3]dioxol-4-yl)-5-methylpyrimidin-2(1H)-one (500 mg, 1.17 mmol) in tetrahydrofuran (1.4 ml) was cooled in an ice bath under argon; a solution of 1 M tetrabutylammonium fluoride in tetrahydrofuran (1.4 ml, 1.90 mmol) was added and the mixture stirred for 2 hrs at room temperature. The crude product was collected by filtration, washed with tetrahydrofuran and purified by flash chromatography (silica gel; methanol: ethyl acetate 1:10) to give 4-amino-1-((3aR, 4R,6R,6aS)-6-(hydroxymethyl)-2,2-dimethyltetrahydrothieno[3,4-d][1,3]dioxol-4-yl-5-methylpyrimidin-2(1H)-one (436 mg, quant). $^1$H NMR (300 MHz, DMSO) δ 7.64 (s, 1H), 7.38 (brs, 1H), 6.85 (brs, 1H), 5.97 (d, J=2.8 Hz, 1H), 5.19 (t, 5.5 Hz, 1H), 4.88 (dd, J=2.8 and 5.35 Hz, 1H), 4.80 (dd. J=3.2 and 5.9 Hz, 1H), 3.67 (m, 1H), 3.54 (m, 1H), 3.47 (td, J=2.8 and 6.4 Hz, 1H), 1.80 (s, 3H), 1.43 (s, 3H), 1.21 (s, 3H).

Synthesis of Nucleotide Targets

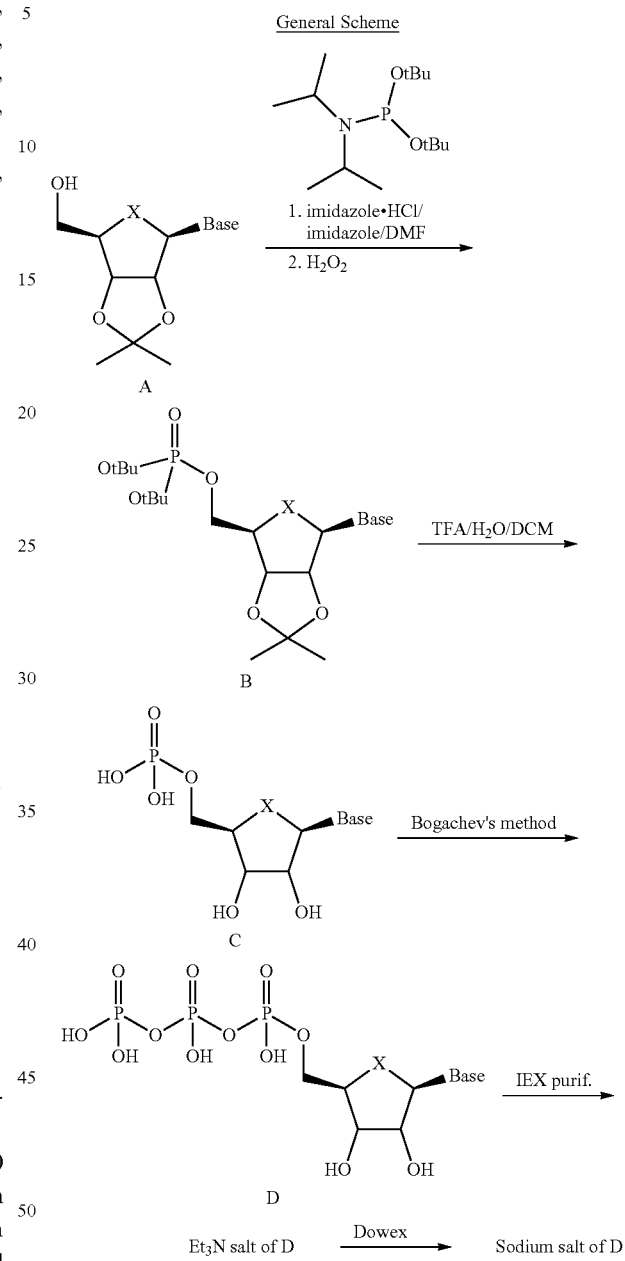

The synthesis of the nucleoside 5'-triphosphates is shown above. Nucleoside A is reacted with phosphoramidite reagent in presence of imidazole.HCl/imidazole in dimethylformamide followed by subsequent oxidation of the phosphorous with H$_2$O$_2$ to give B in good yield (after purification by column chromatography on silica gel, typically 60 to 83% yield). Cleavage of the protecting groups by treatment with trifluoroacetic acid in H$_2$O/dichloromethane gives the monophosphate C, typically in quantitative yield. Finally the triphosphate is obtained using a method developed by Bogachev (Bogachev, V. S. Synthesis of deoxynucleoside 5'-triphosphates using trifluoroacetic anhydride as activation reagent. *Russ. J. Bioorg. Chem.*, 1996, 22, 599-604).

General Experimental Procedures

Synthesis of B

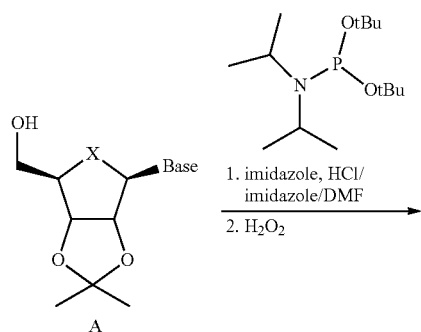

To a solution of A (1 eq.), imidazole.HCl (1.5 eq.) and imidazole (1 eq.) in dimethylformamide (3 ml/mmol of A) is added dropwise di-tert-butyl diisopropylphosphoramidite (1.5 eq.) at room temperature under argon. The reaction mixture is stirred until complete consumption of starting material was observed (LC-MS or TLC) (typically 30-90 min). The reaction mixture is then cooled in an ice-water bath and treated dropwise with 35% $H_2O_2$ (2.6 eq.) The reaction mixture is warmed to room temperature and stirred until complete reaction is observed (LC-MS or TLC); it is then cooled in an ice-water bath and carefully quenched with saturated aqueous sodium thiosulphate. The product is extracted with ethyl acetate; the organic layer is washed with brine, dried over magnesium sulphate, filtered and concentrated under reduced pressure. Purification by column chromatography on silica gel with an appropriate eluent (generally methanol/dichloromethane) gives B, typically in 60 to 85% yield.

Synthesis of C

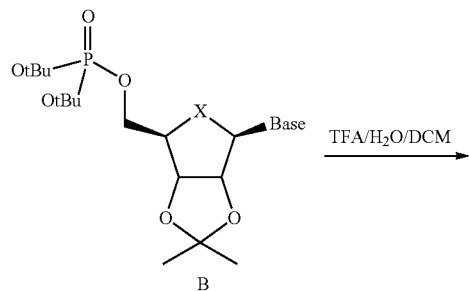

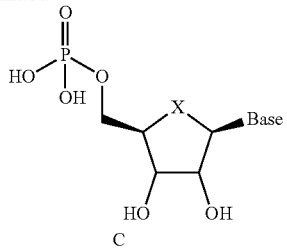

A mixture of B (1 eq.) in dichloromethane (2 ml/mmol of B), water (3 ml/mmol of B) and trifluoroacetic acid (3 ml/mmol of B) is stirred overnight at room temperature. The reaction mixture is concentrated under reduced pressure (water bath <50° C.) to give C, typically in quantitative yield.

Synthesis of D

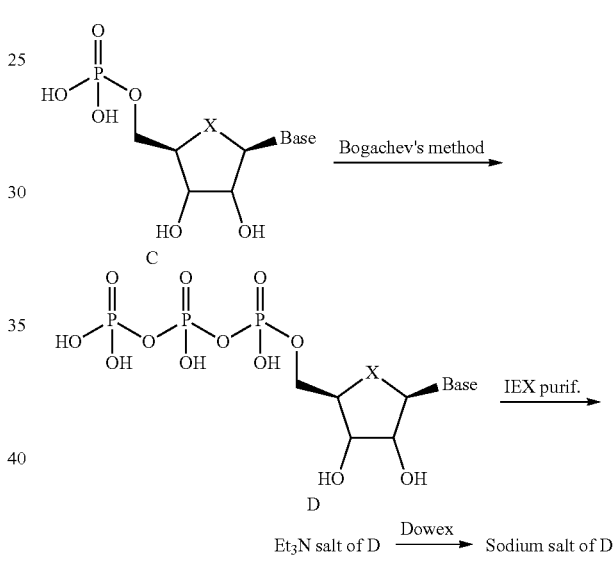

A cooled solution (ice-water bath) of trifluoroacetic anhydride (5 eq.) in acetonitrile (0.3 ml/mmol of trifluoroacetic anhydride) is added dropwise to a cooled suspension of C (1 eq.) in acetonitrile (4 ml/mmol of C), triethylamine (1 eq.) and N,N-dimethylaniline (4 eq.) under argon. The reaction is then allowed to warm to room temperature, stirred at RT for 30 min and the volatiles are removed under reduced pressure.

The resulting syrup is dissolved in acetonitrile (4 ml/mmol of C), cooled in an ice-water bath and 1-methylimidazole (3 eq.) and triethylamine (5 eq.) are added under argon. The reaction mixture is stirred for 15 min and then allowed to warm to room temperature.

A solution of tris(tetrabutylammonium)pyrophosphate (1.5 eq.) in acetonitrile (1 ml/mmol of pyrophosphate) under argon is added dropwise at room temperature and the mixture is stirred at room temperature for 45 min. The reaction is then quenched with deionised water (ca. 10-15 ml/mmol of C) and stirred for 1 h. The mixture is washed with chloroform (3×10 ml), the combined organic layers are back extracted once with deionised water (5 ml). The combined aqueous layers are directly loaded onto a column packed with DEAE Sepharose fast flow and eluted with a gradient of triethylammonium bicarbonate buffer from 0.01 M to 0.5 M. The product-containing fractions are combined and freeze dried. The resulting nucleoside triphosphate triethylamine salt is dissolved in deionised water and then subjected to a Dowex 50 W 8 ion exchange column. The fractions that show UV activity are combined and the water is removed by freeze drying to give the nucleoside 5'-triphosphate as its sodium salt.

((2R,3S,4R,5R)-5-(2,4-dioxo-3,4-dihydropyrimidin-1(2H)-yl)-3,4-dihydroxytetra-hydrothiophen-2-yl) methyl Triphosphate Sodium Salt Using the method described above for the conversion of B to C, 14 (1.25 g, 2.58 mmol) was converted to 15 (0.9 g quant). $^1$H NMR (300 MHz, D$_2$O) δ 8.13 (d, J=7.8 Hz, 1H), 5.81 (d, J=5.5 Hz, 1H), 5.76 (d, J=8.3 Hz, 1H), 4.24 (dd, J=4.1 and 6.0 Hz, 1H), 4.11 (t, J=4.1 Hz, 1H), 3.98 (m, 2H), 3.43 (m, 1H).

Using the method described above for the conversion of C to D, 15 (200 mg, 0.59 mmol) was converted to 4'-Thio-UTP (215 mg, 62% (if 4Na+ salt)). $^1$H NMR (300 MHz, D$_2$O) δ 8.14 (d, J=8.3 Hz, 1H), 5.85 (d, J=6.4 Hz, 1H), 5.81 (d, J=7.8 Hz, 1H), 4.31 (dd, J=3.7 and 6.4 Hz, 1H), 4.24 (t, J=3.7 Hz, 1H), 4.12 (m, 1H), 4.00 (m, 1H), 3.44 (m, 1H). $^{31}$P NMR (300 MHz, D$_2$O) δ −8.57 (d), −10.91 (d), −22.09 (t). HPLC/MS: RT 9.638 min, m/z 501 (M+H)$^+$.

(((2R,3S,4R,5R)-5-(4-amino-5-methyl-2-oxopyrimi-din-1(2H)-yl)-3,4-dihydroxytetra-hydrothiophen-2-yl)methyl triphosphate) Sodium Salt

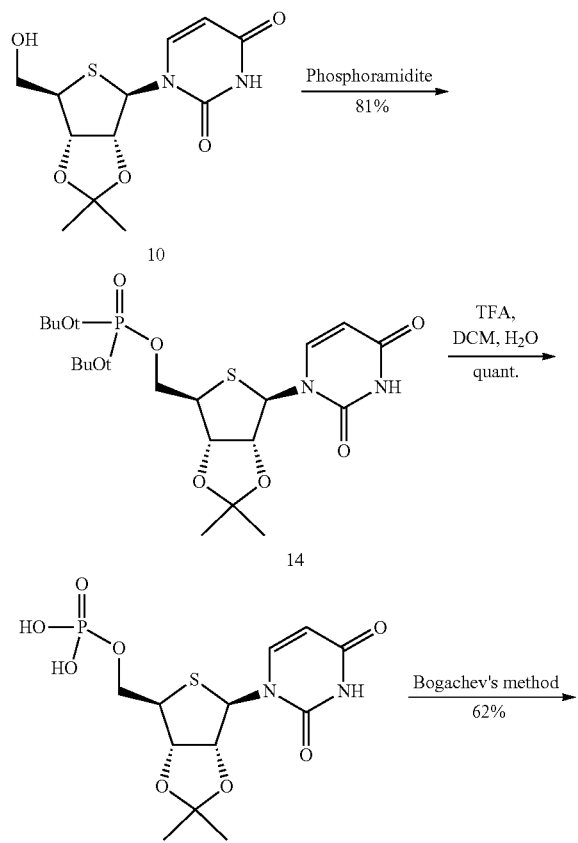

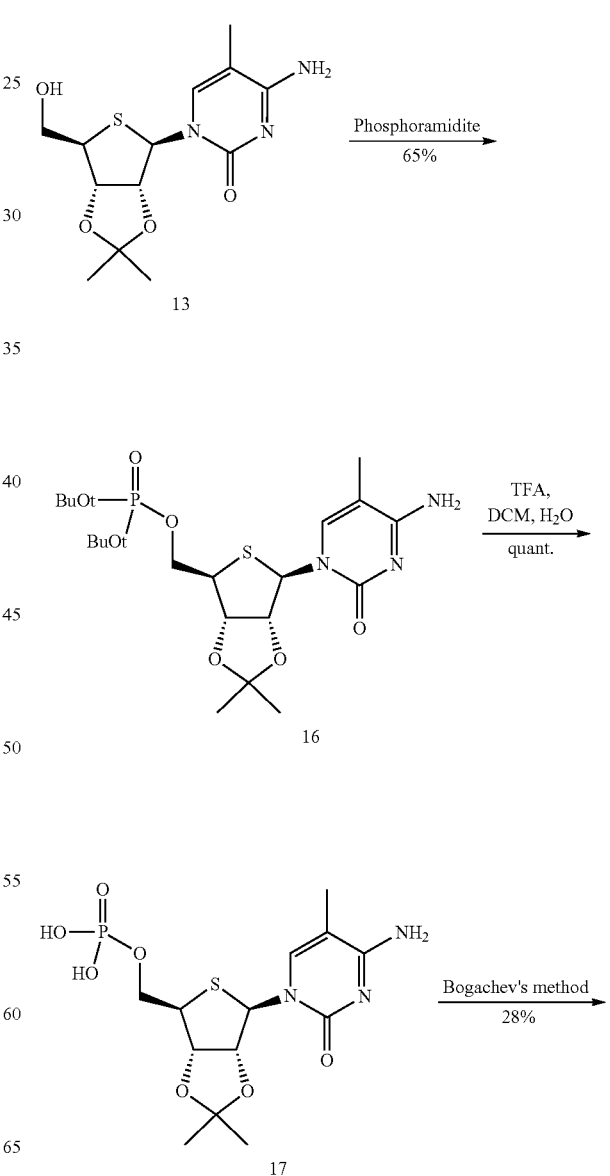

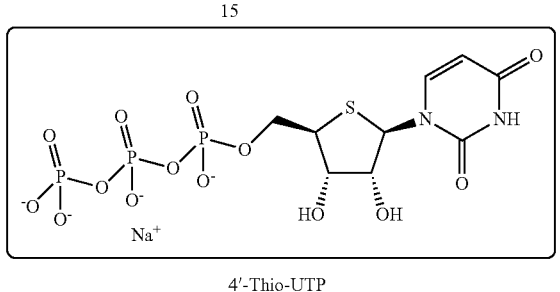

4'-Thio-UTP

Using the method described above for the conversion of A to B, 10 (935 mg, 3.11 mmol) was converted to 14 (1.25 g, 81%). $^1$H NMR (300 MHz, CDCl$_3$) δ 8.38 (brs, 1H), 7.74 (d, J=8.3 Hz, 1H), 6.05 (s, 1H), 5.79 (d, J=8.3 Hz), 4.85 (m, 2H), 4.19 (m, 2H), 3.83 (t, J=5.0 Hz, 1H), 1.54 (s, 3H), 1.49 (s, 18H), 1.31 (s, 3H).

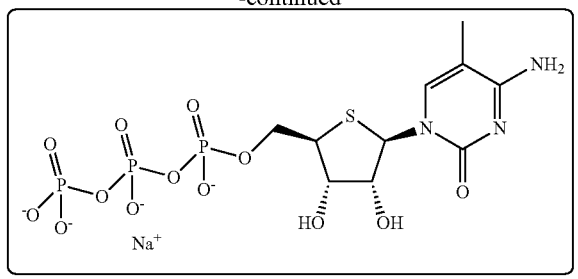

4'-Thio-5-MethylCTP

Using the method described above for the conversion of A to B, 13 (400 mg, 1.28 mmol) was converted to 16 (910 mg 65%). $^1$H NMR (300 MHz, CDCl$_3$) δ 8.19 (brs, 2H), 7.45 (s, 1H), 5.92 (d, J=2.1 Hz, 1H), 4.98 (dd, J=1.8 and 6.0 Hz, 1H), 4.95 (dd, J=2.3 and 5.5 Hz, 1H), 4.24 (m, 2H), 3.80 (td, J=1.8 and 6.0 Hz, 1H), 1.99 (s, 3H), 1.56 (s, 3H), 1.49 (s, 9H), 1.48 (s, 9H), 1.29 (s, 3H).

Using the method described above for the conversion of B to C, 16 (480 mg, 0.977 mmol) was converted to 17 (350 mg, quant). $^1$H NMR (300 MHz, D$_2$O) δ 8.16 (s, 1H), 5.80 (d, J=6.0 Hz, 1H), 4.25 (dd, J=4.1 and 5.5 Hz, 1H), 4.10 (t, J=4.6 Hz, 1H), 4.00 (m, 2H), 3.45 (m, 1H), 1.92 (s, 3H). $^{31}$P NMR (300 MHz, D$_2$O) δ 0.41.

Using the method described above for the conversion of C to D, 15 (300 mg, 0.849 mmol) was converted to 4'-Thio-5-MethylCTP (136 mg, 28% (if 4Na+ salt)). $^1$H NMR (300 MHz, D$_2$O) δ 7.84 (s, 1H), 5.85 (d, J=6.4 Hz, 1H), 4.23 (m, 2H), 4.09 (m, 1H), 3.97 (m, 1H), 3.40 (m, 1H), 1.82 (s, 3H). $^{31}$P NMR (300 MHz, D$_2$O) δ −8.96 (d), −11.00 (d), −22.28 (t), $^{13}$C NMR (300 MHz, D$_2$O) δ 165.52 (Cq), 158.09 (Cq), 139.80 (CH), 105.40 (Cq), 77.26 (CH), 73.25 (CH), 66.06 (CH), 64.04 (CH2), 50.09 (CH), 12.33 (CH3). HPLC/MS: RT 10.280 min, m/z 514 (M+H)$^+$.

Using a procedure analogous to the preceding synthesis of 4'-Thio-5-MethylCTP, but substituting 13.1 for 13, 4'-Thio-CTP can be made.

((2R,3S,4R,5R)-5-(6-amino-9H-purin-9-yl)-3,4-dihydroxytetrahydrothiophen-2-yl)methyl Triphosphate Sodium Salt

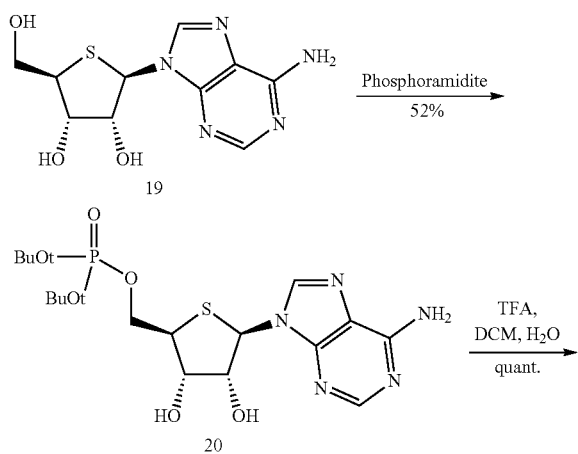

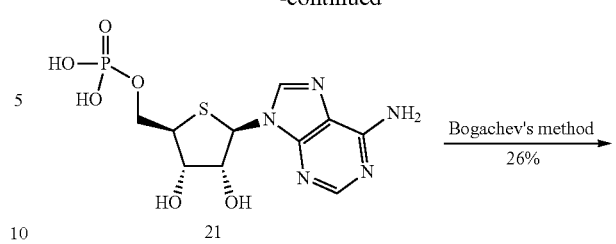

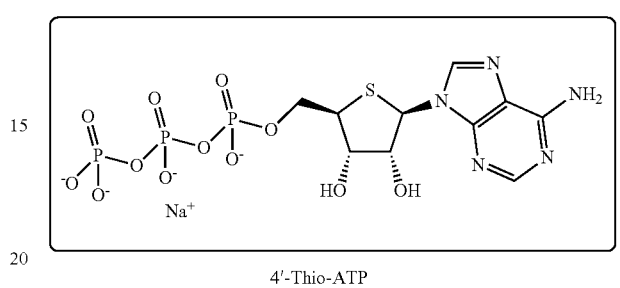

4'-Thio-ATP

Using the method described above for the conversion of A to B, 19 (504 mg, 1.81 mmol) was converted to 20 (444 mg, 52%), $^1$H NMR (300 MHz, CDCl$_3$) δ 8.24 (s, 1H), 8.19 (brs, 1H), 7.71 (brs, 1H), 7.09 (s, 1H), 6.20 (brs, 2H), 6.01 (d, J=5.0 Hz, 1H), 4.76 (m, 1H), 4.50 (m, 1H), 4.23 (m, 2H), 3.77 (m, 1H), 1.48 (s, 18H).

Using the method described above for the conversion of B to C, 20 (430 mg, 0.904 mmol) was converted to 21 (330 mg quant). $^1$H NMR (300 MHz, D$_2$O) δ 8.64 (s, 1H), 8.26 (s, 1H), 5.86 (d, J=5.5 Hz, 1H), 4.54 (m, 1H) 4.26 (m, 1H), 4.06 (m, 2H), 3.54 (m, 1H).

Using the method described above for the conversion of C to D, 21 (82 mg, 0.162 mmol) was converted to 4'-Thio-ATP (35 mg, 26% (if 4Na+ salt)). $^1$H NMR (300 MHz, D$_2$O) δ 8.49 (s, 1H), 8.03 (s, 1H), 5.76 (d, J=5.6 Hz, 1H), 4.54 (dd, J=3.7 and 5.6 Hz, 1H), 4.35 (t, J=4.1 Hz, 1H), 4.13 (m, 2H), 3.54 (dd, J=4.1 and 8.7 Hz, 1H). $^{31}$P NMR (300 MHz, D$_2$O) δ −9.07 (d), −10.81 (d), −22.15 (t). HPLC/MS: RT 10.467 min, m/z 524 (M+H)$^+$.

5-((3R,4S,5R)-3,4-dihydroxy-5-(hydroxymethyl)tetrahydrothiophen-2-yl)pyrimidine 2,4(1H,3H) dione (4'-S-Pseudouridine). This compound can be made following the scheme below using procedures known to those skilled in the art.

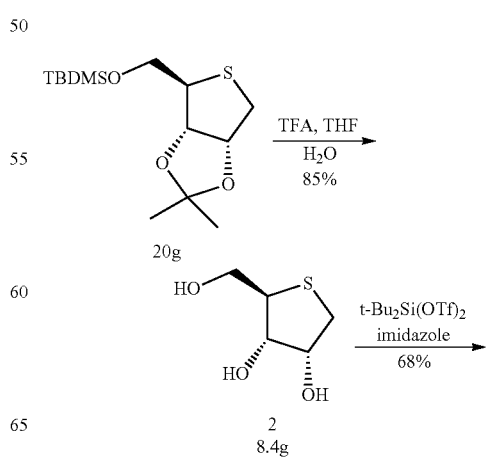

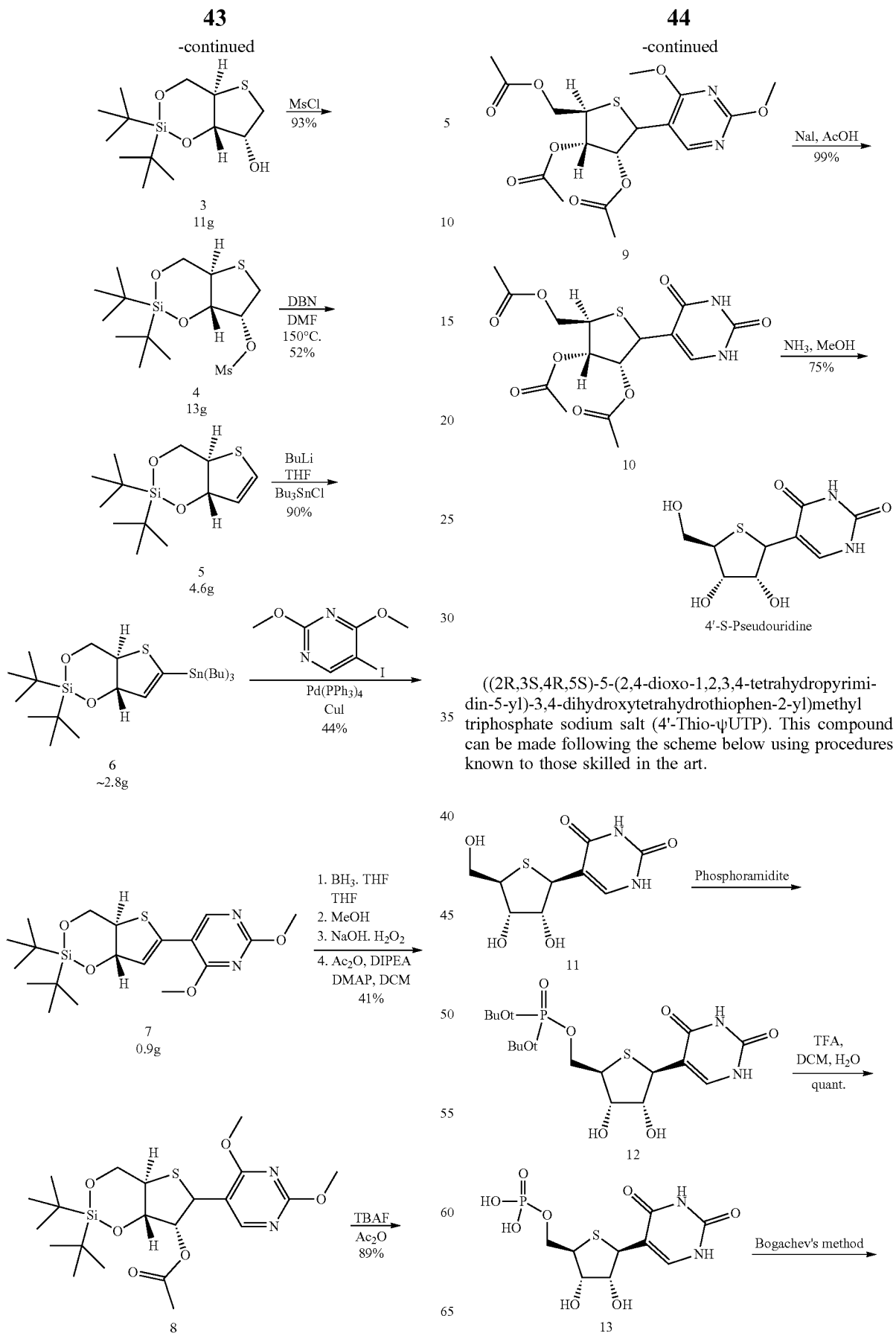
((2R,3S,4R,5S)-5-(2,4-dioxo-1,2,3,4-tetrahydropyrimidin-5-yl)-3,4-dihydroxytetrahydrothiophen-2-yl)methyl triphosphate sodium salt (4′-Thio-ψUTP). This compound can be made following the scheme below using procedures known to those skilled in the art.

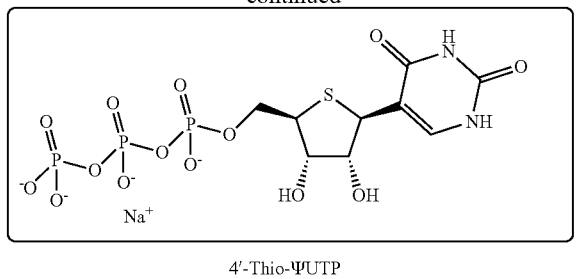

4'-Thio-ΨUTP ((2R,3S,4R,5R)-3,4-dihydroxy-5-(4-oxo-2-thioxo-3,4-dihydropyrimidin-1(2H)-yl)tetrahydrothiophen-2-yl)methyl tetrahydrogen triphosphate (4'-S-2-S-UTP). This compound can be made following the scheme below using procedures known to those skilled in the art.

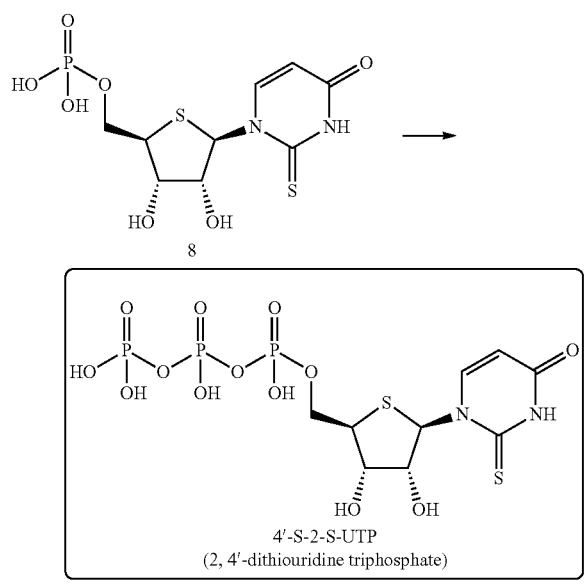

((2R,3S,4R,5R)-5-(2-amino-6-oxo-1H-purin-9(6H)-yl)-3,4-dihydroxytetrahydrothiophen-2-yl)methyl tetrahydrogen triphosphate (4'-S-GTP). This compound can be made following the scheme below using procedures known to those skilled in the art.

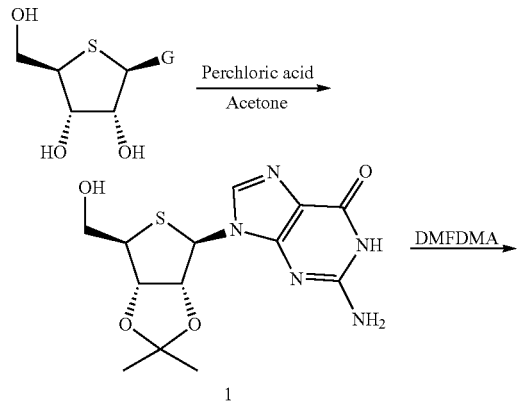

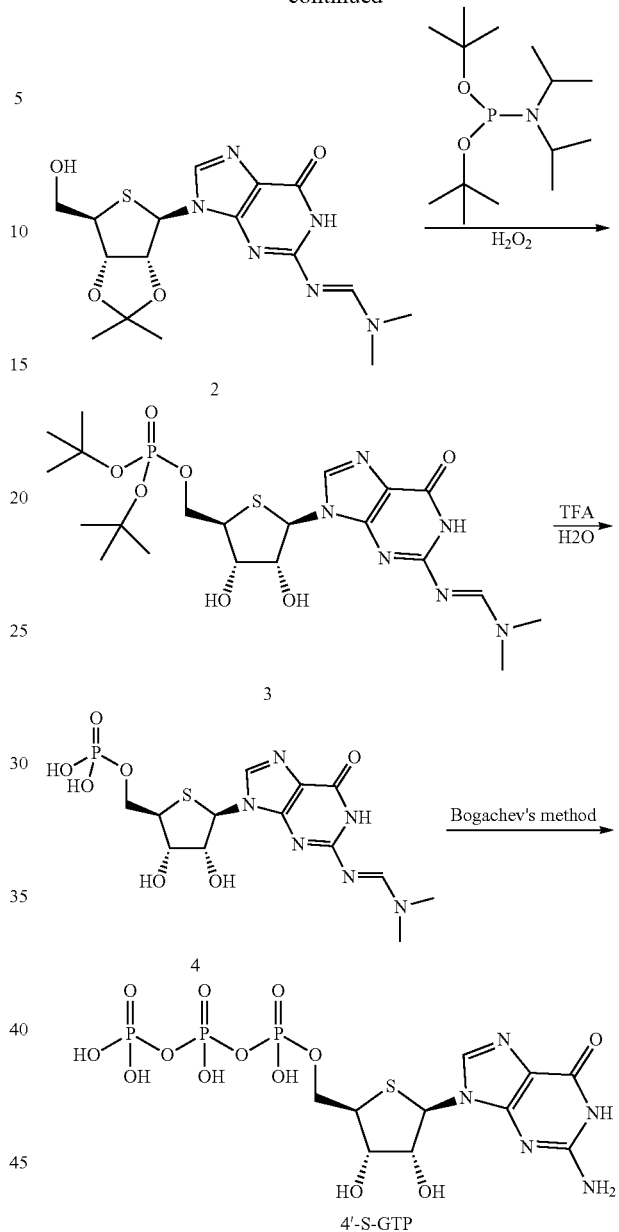

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed, by the invention. All publications and patents cited in this disclosure are incorporated, by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. The recitation of series of numbers with differing amounts of significant digits in the specification is not to be construed as implying that numbers with fewer significant digits given have the same, precision as numbers with more significant digits given.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from actual publication dates which may need to be independently confirmed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A full length mRNA molecule that encodes a full length protein, having a coding region and optionally, one or more non-coding regions, wherein the mRNA is at least 500 nucleotide residues in length; at least 1% of the total mRNA nucleotide residues incorporate a 4'-thio-substituted furanose ring, and up to 20% of the total mRNA nucleotide residues incorporate a 4'-thio-substituted furanose ring, and wherein the mRNA, upon delivery in vivo, produces a protein encoded by the coding region.

2. The mRNA molecule of claim 1, wherein at least 5% of the total mRNA nucleotide residues incorporate a 4'-thio-substituted furanose ring.

3. The mRNA molecule of claim 1, wherein at least 10% of the total mRNA nucleotide residues incorporate a 4'-thio-substituted furanose ring.

4. The mRNA molecule of claim 1, wherein the non-coding region comprises a poly-A tail, and wherein the poly-A tail comprises 4'-thio-adenosine residues.

5. The mRNA molecule of claim 4, wherein the poly-A tail is at least 90 nucleotide residues in length.

6. The mRNA molecule of claim 1, wherein the mRNA further comprises at least one nonstandard nucleotide residue.

7. The mRNA molecule of claim 1, wherein the molecule comprises at least 5000 nucleotide residues.

8. The mRNA molecule of claim 1, wherein the coding region encodes a full length protein that is a therapeutic protein.

9. The mRNA molecule of claim 8, wherein the therapeutic protein is chosen from erythropoietin, human growth hormone, cystic fibrosis transmembrane conductance regulator (CFTR), insulin, alpha-galactosidase A, alpha-L-iduronidase, iduronate-2-sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), and arginase 1 (ARG1), glucose-6-phosphatase, glucose-6-phosphate translocase, glycogen debranching enzyme, lysosomal alpha-glucosidase, 1,4-alpha-glucan branching enzyme, glycogen phosphorylase, phosphofructokinase, liver phosphorylase, GLUT-2, UDP glycogen synthase, alpha-L-iduronidase, iduronate sulfate silfatase, heparan sulfate sulfamidase, alpha-N-acetylglucose amidase, alpha-glucosaminid-N-acetyltransferase, N-acetylglucosamine-6-sulfate sulfatase, apolipoprotein E, low density lipoprotein receptor (LDLR), Factor VIII, Factor IX, spinal motor neuron 1 (SMN1), phenylalanine hydroxylase, propionyl-CoA carboxylase, porphobilinogen deaminase, pethylmalonyl-CoA mutase, urate oxidase, C1 esterase inhibitor, and acid alpha-glucosidase.

10. A composition comprising at least one mRNA molecule of claim 1 and a carrier that is a lipid nanoparticle or a polymer.

11. The composition of claim 10, wherein the carrier is a lipid nanoparticle that comprises one or more cationic lipids selected from XTC (2,2-dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-di((9Z,12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003, ICE, HGT5000, cis or trans HGT5001, DOTAP (1,2-dioleyl-3-trimethylammonium propane), DOTMA (1,2-di-O-octadecenyl-3-trimethylammonium propane), DLinDMA, DLin-KC2-DMA, and C12-200.

12. The composition of claim 10, wherein the carrier is a lipid nanoparticle that comprises one or more helper lipids selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), and cholesterol.

13. The composition of claim 10, wherein the carrier is a lipid nanoparticle that comprises a pegylated lipid.

14. The composition of claim 10, wherein the lipid nanoparticle comprises one or more cationic lipids, one or more helper lipids, and a pegylated lipid.

15. The composition of claim 10, wherein the carrier comprises a polymer.

16. The composition of claim 15, wherein the polymer is polyethyleneimine.

17. A method of producing a protein in vivo, comprising administering the mRNA of claim 1 to a subject.

* * * * *